(12) United States Patent
Walther et al.

(10) Patent No.: US 12,408,898 B2
(45) Date of Patent: Sep. 9, 2025

(54) BIOPSY INSTRUMENTS AND METHODS

(71) Applicant: BibbInstruments AB, Lund (SE)

(72) Inventors: Charles Walther, Lund (SE); Stephan Dymling, Limhamn (SE); Bruno Walther, Löberöd (SE)

(73) Assignee: BibbInstruments AB (SE)

( * ) Notice: Subject to any disclaimer, the term of this patent is extended or adjusted under 35 U.S.C. 154(b) by 970 days.

(21) Appl. No.: 17/283,928

(22) PCT Filed: Oct. 8, 2019

(86) PCT No.: PCT/EP2019/077210
§ 371 (c)(1),
(2) Date: Apr. 8, 2021

(87) PCT Pub. No.: WO2020/074505
PCT Pub. Date: Apr. 16, 2020

(65) Prior Publication Data
US 2021/0330304 A1    Oct. 28, 2021

(30) Foreign Application Priority Data
Oct. 9, 2018 (EP) .................... 18199230

(51) Int. Cl.
A61B 10/02 (2006.01)
A61B 10/04 (2006.01)

(52) U.S. Cl.
CPC .......... A61B 10/0266 (2013.01); A61B 10/04 (2013.01); A61B 2010/0208 (2013.01); A61B 2010/0225 (2013.01)

(58) Field of Classification Search
CPC .......... A61B 10/02–06; A61B 2010/0208–045
See application file for complete search history.

(56) References Cited

U.S. PATENT DOCUMENTS 5,810,806 A * 9/1998 Ritchart ............. A61B 10/0266
606/41
2006/0074343 A1   4/2006 Hibner
(Continued)

FOREIGN PATENT DOCUMENTS

| JP | 2017 536146 A | 12/2017 |
|----|---------------|---------|
| WO | 93/07819 A2 | 4/1993 |

(Continued)

Primary Examiner — Jennifer Robertson
Assistant Examiner — Nidhi N Patel
(74) Attorney, Agent, or Firm — Condo Roccia Koptiw LLP

(57) ABSTRACT

A biopsy instrument (1) comprising a base member (10) which extends from a proximal end (10a) to a distal end (10b) along a central geometrical axis (A), wherein at least a distal end portion (10b') of the base member (10) is shaped as an elongated hollow tube (10), the distal end (10b) being intended to be at least partly inserted into a tissue (50) from which a biopsy is to be obtained, wherein the hollow tube (10) is provided with a distally facing circular cutting edge (11) defining a mouth (10c) of the distal end (10b) of the hollow tube (10), wherein the hollow tube (10) has, at a distal portion (10b') of the hollow tube (10), a hollow elongated tubular sample acquiring portion (10b') having a smooth interior surface (12). The disclosure also relates to a kit of parts and a method of acquiring a biopsy.

10 Claims, 18 Drawing Sheets

(56) References Cited

U.S. PATENT DOCUMENTS

| | | | | |
|---|---|---|---|---|
| 2009/0118641 A1* | 5/2009 | Van Dam | ........... | A61B 10/0266 |
| | | | | 600/567 |
| 2010/0130850 A1 | 5/2010 | Pakter | | |
| 2010/0152756 A1 | 6/2010 | Mark | | |
| 2010/0312140 A1* | 12/2010 | Smith | ................ | A61B 10/0275 |
| | | | | 600/566 |
| 2013/0060160 A1* | 3/2013 | Heier | ............... | A61B 5/150992 |
| | | | | 600/573 |
| 2013/0223702 A1 | 8/2013 | Holsing et al. | | |
| 2015/0272556 A1* | 10/2015 | Lee | ........................ | A61B 10/04 |
| | | | | 600/566 |
| 2016/0346519 A1 | 12/2016 | Bagwell et al. | | |
| 2018/0042588 A1* | 2/2018 | Baillargeon | ....... | A61B 10/0283 |
| 2018/0161053 A1* | 6/2018 | Matsumoto | ............... | F16C 1/20 |
| 2021/0045720 A1* | 2/2021 | Kadamus | ........... | A61B 10/0233 |

FOREIGN PATENT DOCUMENTS

| | | |
|---|---|---|
| WO | 9508291 A1 | 3/1995 |
| WO | WO 200197702 | 12/2001 |
| WO | WO 201166470 | 6/2011 |
| WO | WO 2016054063 A1 | 4/2016 |
| WO | WO 2016/154170 A1 | 9/2016 |
| WO | 2019/155472 A1 | 8/2019 |

\* cited by examiner

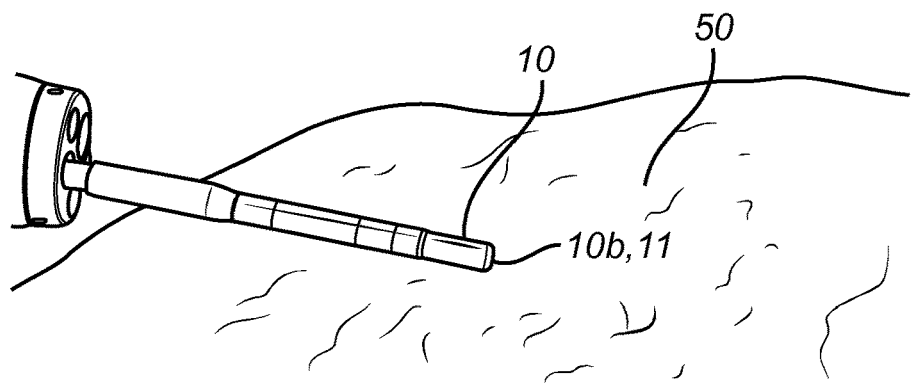
*Fig. 13a*
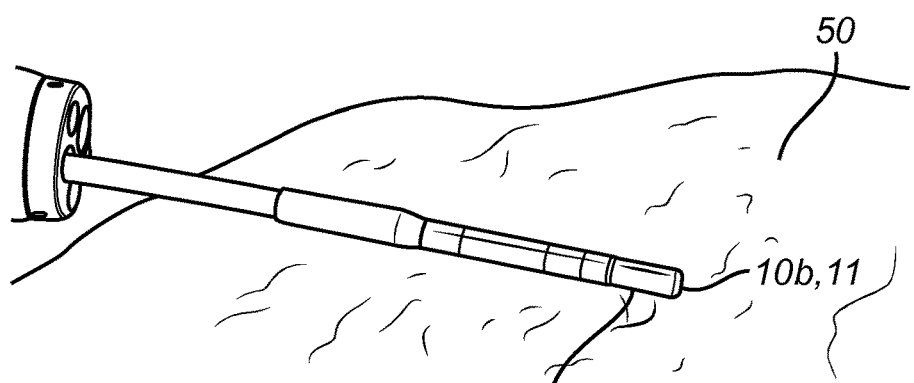
*Fig. 13b*
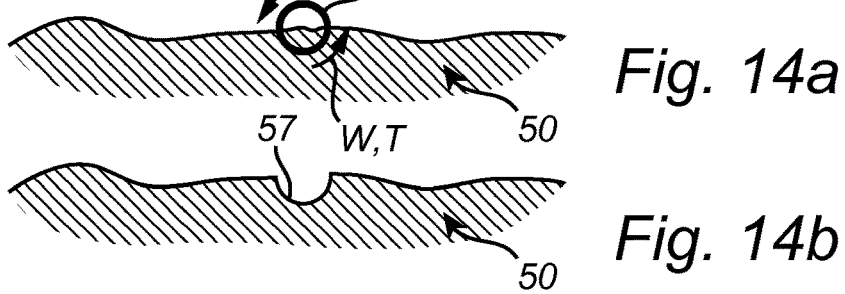
*Fig. 14a*
*Fig. 14b*
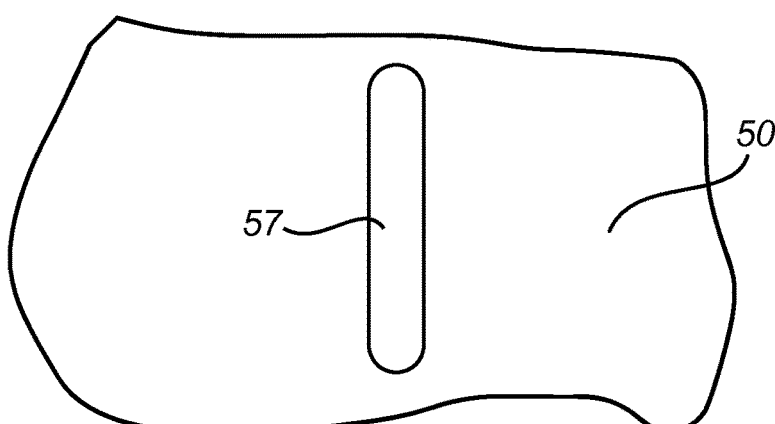
*Fig. 14c*

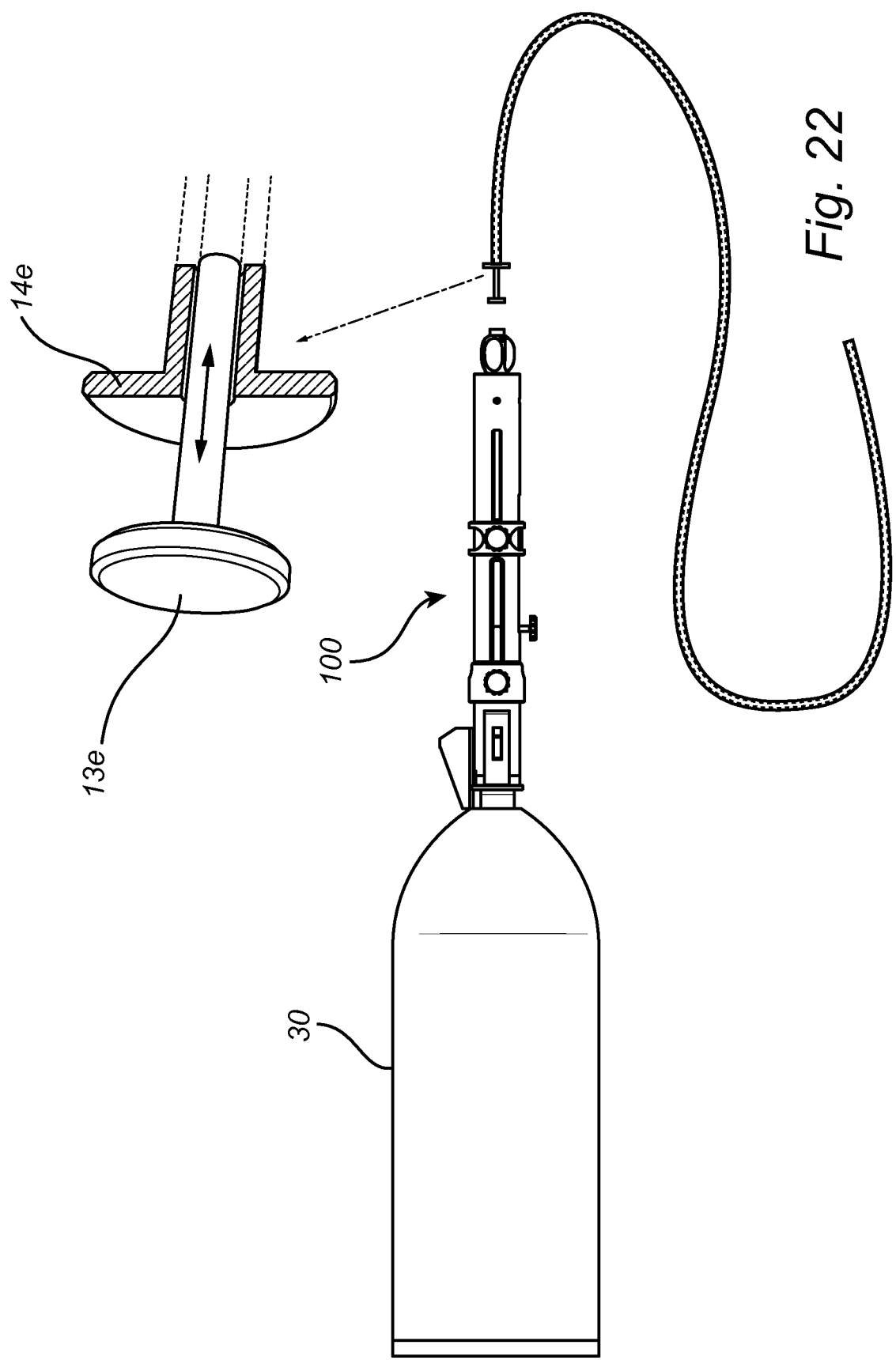

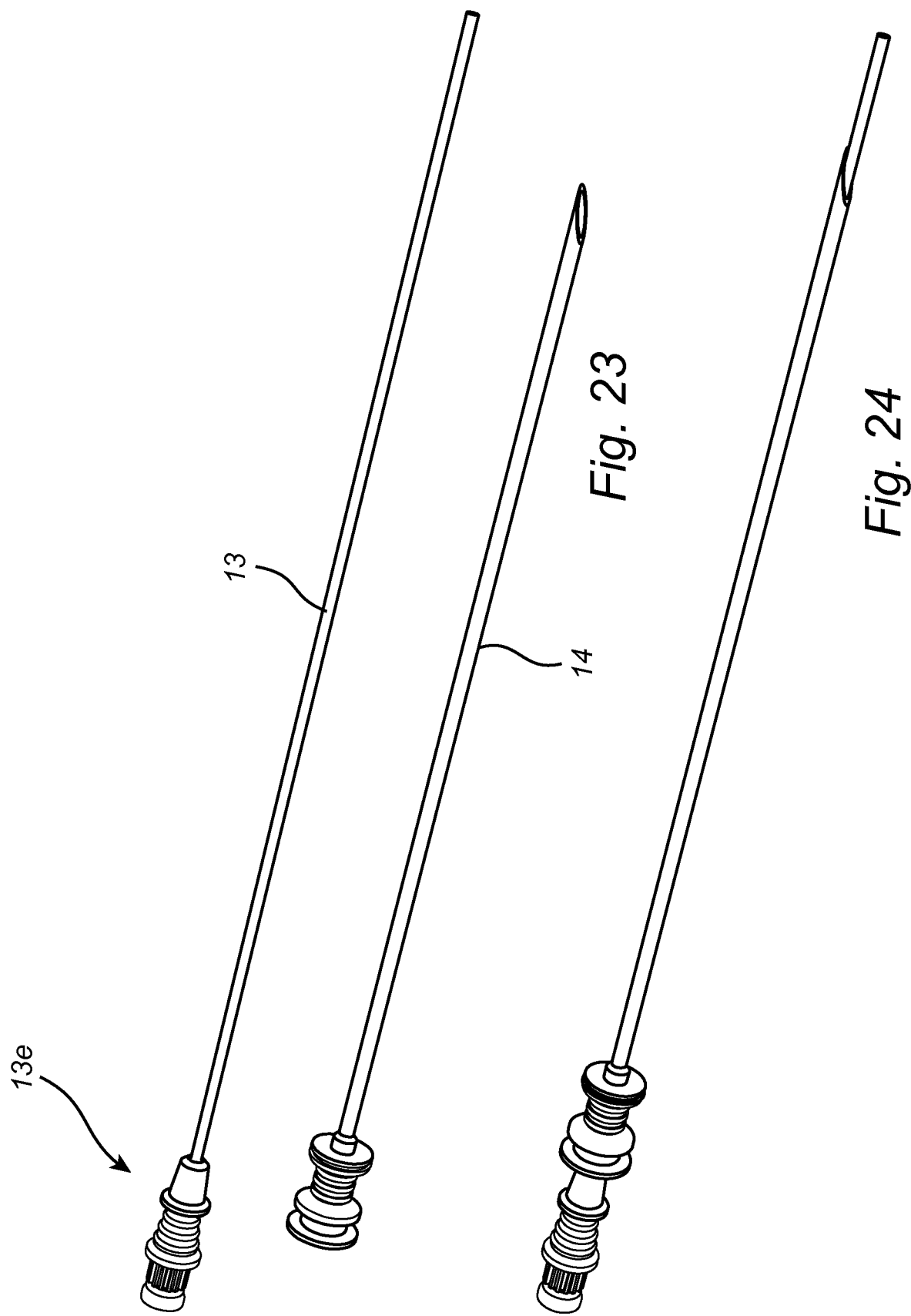

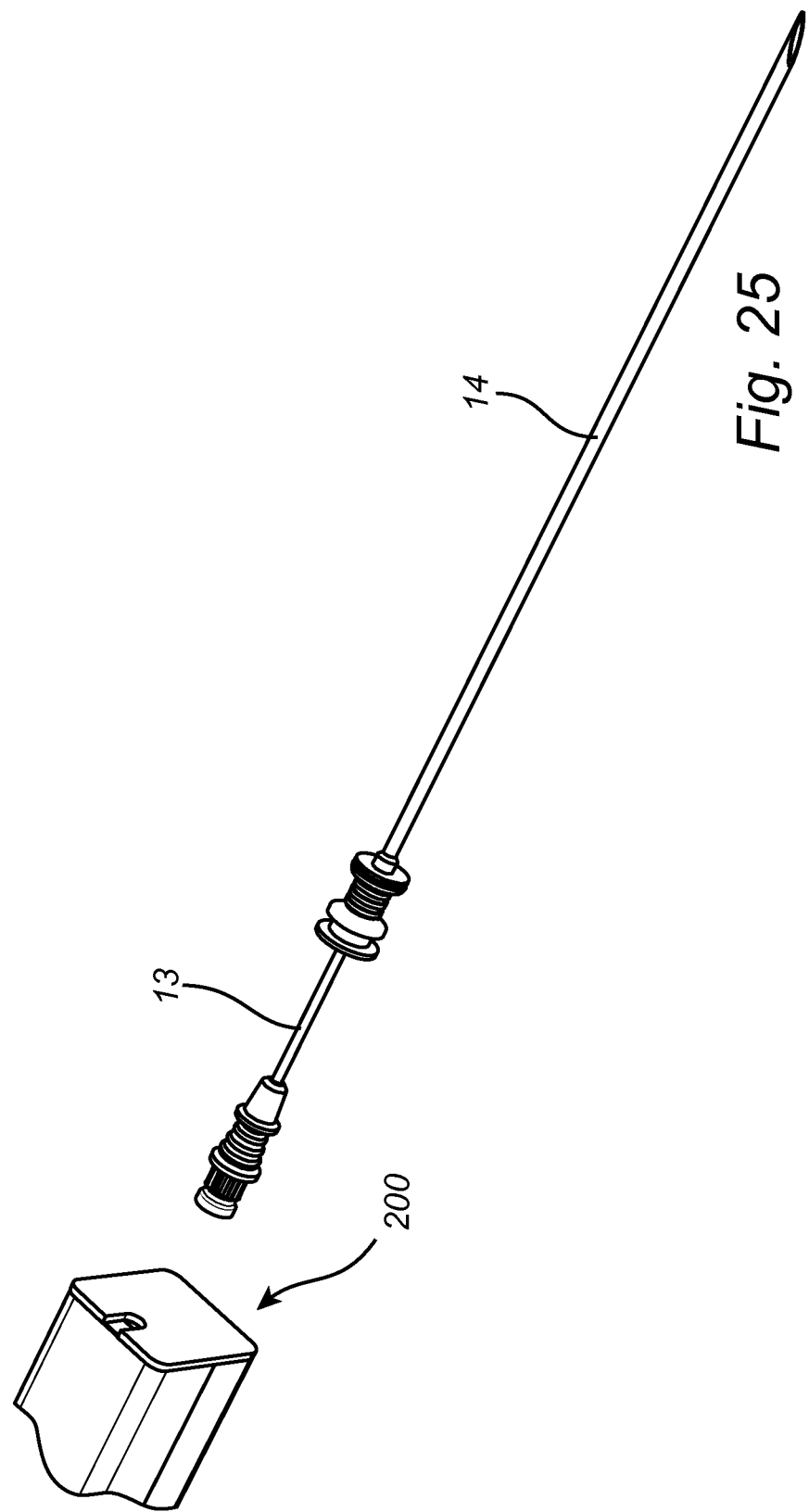

BIOPSY INSTRUMENTS AND METHODS

CROSS REFERENCE TO RELATED APPLICATIONS

This application is the National Stage Entry under 35 U.S.C. § 371 of Patent Cooperation Treaty Application No. PCT/EP2019/077210, filed Oct. 8, 2019, which claims priority from EP Application Serial No. 18199230.6, filed Oct. 9, 2018, the contents of each of which are hereby incorporated by reference herein in their entireties.

FIELD OF INVENTION

The invention relates to a biopsy instrument.
The invention also relates to a kit of parts.
The invention also relates to a method of acquiring a biopsy.

TECHNICAL BACKGROUND

A biopsy is a medical test commonly performed by a physician involving sampling of cells or tissues for examination. The biopsy is often acquired using a biopsy instrument inserted into a patient's body via an endoscope. A large variety of endoscopic biopsy instruments are commercially available today, the majority of which are biopsy forceps that pinch off the tissue sample, or fine needles that aspirate cells by applying under-pressure.

For some diagnostic purposes, the millimetre-sized samples retrievable using forceps are sufficient, but for some types of lesions and tumours, such as comparably deep lesions or deep growing tumours, such a small and superficial sample is inadequate for making a diagnosis. The fine needles are often capable of reaching deeper tumours but are only capable of retrieving small amounts of dispersed cells, thereby limiting the diagnostic abililty.

When taking a tissue sample with an endoscopic biopsy instrument, the instrument is inserted in a working channel of an endoscope, and advanced to the biopsy site. After the tissue sample has been obtained, the endoscopic biopsy instrument is retracted from the endoscope such that the tissue sample can be placed in a storage unit for evaluation by a pathologist.

Biopsy is today the primary diagnostic tool for determining malignancy of neoplastic growths. As the methods of cancer treatment have been improved and refined, the number of biopsies required for diagnostics have increased. Before the optimal method of treatment can be determined, the spread and density of the malignant cells need to be assessed, which in for example the diagnostics of laryngeal or esophageal cancer may require 20-30 biopsies, a process which is time consuming and incommodious for both the patient and the physician. Apart from that, the forceps separate the tissue sample from the body of the patient by tearing, which risks damaging the tissue sample and makes it more difficult to evaluate the biopsy. The fine needles supply small amounts of cells that cannot be prepared by routine histological methods and typically also require more advanced endoscopic equipment with ultrasound.

In this context one may mention WO201166470 which discloses an endoscopic biopsy instrument having a kind of forceps with a storage lumen for multiple biopsies. The biopsies are transported upwardly into the storage lumen by the use of a suction which is applied when a sample is retrieved.

Another technology sometimes used is the provision of a needle having a closed distal end and instead having an opening in the circumferential surface close to the distal end. In such needles there is made use of a suction which sucks a portion of the tissue into the opening in the circumferential surface. Inside the needle there is provided a reciprocating cutting tool which passes back and forth past the opening and cuts the portion of the tissue being inside the circumferential surface. Examples of this technology is e.g. shown in US20100152756 and US20060074343.

In WO200197702 there is disclosed a biopsy instrument in which an outer needle or cannula inserted into a tissue and brought into contact with a lesion whereby a continuous suction applied at the proximal end of the cannula is used to fixate the lesion to the distal end of the cannula. While maintaining a suction force keeping the lesion in place, a second medical device, such as a biopsy needle or a cryo-probe, is inserted through an airtight seal at the proximal end of the instrument and through the cannula to the lesion. In US 2013/0223702 A1 there is also disclosed various kinds of biopsy instruments using forceps, an auger or vacuum to draw a tissue sample into the instrument.

A problem with the above disclosed technologies is also that they rely on the application of a suction, which renders the instrument complicated.

It would therefore be advantageous to have a biopsy instrument which allows for a straight-forward and robust design and which is capable of retrieving tissue samples in an amount being sufficient for diagnostics in a short time.

SUMMARY OF INVENTION

It is an object of the invention to provide a biopsy instrument which allows for a straight-forward and robust design and which is capable of retrieving tissue samples in an amount being sufficient for diagnostics in a short time.

This object has been achieved by a biopsy instrument comprising a base member which extends from a proximal end to a distal end along a central geometrical axis, wherein at least a distal end portion of the base member is shaped as an elongated hollow tube, the distal end being intended to be at least partly inserted into a tissue from which a biopsy is to be obtained, wherein the base member is capable of transferring a force along the central geometrical axis such that a movement of the proximal end along the central geometrical axis is transferred to a movement of the distal end along the central geometrical axis, and of transferring a torque about the central geometrical axis such that a rotation and a torque applied by a motor at the proximal end about the central geometrical axis is transferred from the proximal end to the distal end thereby rotating the distal end about the central geometrical axis, wherein the hollow tube is provided with a distally facing circular cutting edge defining a mouth of the distal end of the hollow tube, wherein the hollow tube has, at a distal portion of the hollow tube, a hollow elongated tubular sample acquiring portion having a smooth interior surface, wherein the smooth interior surface is smooth to such an extent that when a reference biopsy is to be acquired, the cutting edge and the distal end of the hollow tube is configured to be advanced along the central geometrical axis into a tissue while being rotated by being motor driven at its proximal end and thereby cutting a core of the tissue which, due to the advancement of the hollow tube, enters relative to the hollow tube through the mouth into the sample acquiring portion of the hollow tube with a circumferential outer surface of the core at least partly abutting the smooth interior surface of the sample acquiring portion, where-after the hollow tube is retracted from the tissue while being rotated by being motor driven at its proximal end whereby the core of the tissue is detached from the tissue by a pulling force due to the retraction of the hollow tube and due to an adhesive force formed at an interface between the smooth interior surface and the circumferential outer surface of the core which force keeps the core inside the sample acquiring portion having the smooth interior surface. The adhesive force in combination with rotation produces a rotation of the sample at the most distal end when the sample is pulled back, in effect releasing it from the tissue by the increasingly thinning and twisted thread produced by the rotation of the biopsy.

The biopsy instrument is advantageous compared to prior art biopsy instruments in that it makes it possible to retrieve tissue samples in an amount being sufficient for diagnostics in a comparably short time. The biopsy instrument is capable of retrieving a plurality of tissue samples directly one after the other without a previous sample needs to be harvested. A first sample is in a controlled manner pushed further into the hollow tube towards the proximal end by the core of the second sample when the distal end is advanced into the tissue for a second time. The fact that the hollow tube is provided with a smooth interior surface being smooth to such an extent that the core adhesively by itself, due to the smooth surface and the presence of liquid in the tissue, becomes adhered to the inside of the hollow tube makes it possible to retrieve samples with a minimum of damage to the sample and still allow for the cutting edge and distal end to be drilled into and out of the tissue thereby reducing discomfort for the patient. As the core becomes adhered to the inside of the elongated tubular member, the core will at the mouth of the elongated tubular member be twisted and be released from the sample site. Compared to prior art biopsy instruments there is with the inventive biopsy instrument no need for any hooks or the like on the inside of the instrument, which hooks has the drawback that they are difficult to combine with drilling in and out of the tissue and still avoiding to damage the samples. The fact that the inventive biopsy instrument is so gentle to the samples also allows for the samples to be harvested in a controlled manner such that each sample is still uniquely identifiable and still undamaged. This allows for the physician to keep any information provided by the stratigraphy and/or position of respective sample, which in turn may be used to increase the amount of data provided by the biopsy, which in turn may increase the accuracy of the diagnosis ultimately provided.

It may be noted that in the above it is referred to a reference sample. This notion of referring to a reference sample when defining a reference for the smoothness is used since the biopsy instrument may in actual biopsy sampling be used in accordance with a number of different methods. It may e.g. be used in accordance with one method where the biopsy instrument is actually used as referred to in the above and as e.g. shown in FIGS. 3-5, i.e. where the distal end is advanced a distance into the tissue and thereafter is retracted. However, the biopsy instrument may in accordance with another method be used to move along the surface of the tissue from which the biopsy is to be obtained as e.g. shown in FIGS. 13*a-b* and 14*a-c*. In the user method shown in FIGS. 3 and 4, the distal end is fully inserted into the tissue in the sense that the distal end is inserted with the complete circumference inserted into the tissue whereby an adhesive force larger than breaking force needed to detach the core from the tissue is formed. In the method shown in FIGS. 13*a-b* and 14*a-c*, the distal end is only partly inserted into the tissue in the sense that the distal end is inserted with only a portion of the complete circumference being inserted into the tissue. The smoothness of the surface has advantages in both methods but the adhesive force provided by the smoothness is clearly pronounced and observable by the detachment of the core from the remainder of the tissue when performing the reference sample as referred to above. It may be noted that the reference sample refers to a sample performed in healthy tissue.

The surface is preferably smooth to such an extent that when performing a reference sample with a biopsy instrument of the above kind, a core is, during retraction of the hollow tube, detached from the tissue in case the distal end has been inserted into the tissue a distance being the same or greater than an inner diameter of the mouth. However, it is in many cases preferred that the surface is smooth to such an extent that when performing a reference sample with a biopsy instrument of the above kind, a core is, during retraction of the hollow tube, detached from the tissue in case the distal end has been inserted into the tissue a distance being 1,3 times or greater than an inner diameter of the mouth. However, it is in many more preferred that the surface is smooth to such an extent that when performing a reference sample with a biopsy instrument of the above kind, a core is, during retraction of the hollow tube, detached from the tissue in case the distal end has been inserted into the tissue a distance being at least 1,7 times or greater than an inner diameter of the mouth. The above applies at least for inner diameters being between 1-5 mm.

The hollow tube has preferably an extension and is provided with said smooth surfaces along a length from the distal end towards the proximal end, the extension having at least a length allowing for at least two, preferably at least three, reference samples of the above disclosed kind to be acquired one after the other.

It may be noted that the base member may from a bending perspective in accordance with one embodiment be rigid and extend with the central geometrical axis extending along a straight line. Such a rigid biopsy instrument is typically used as a separate biopsy instrument. In accordance with another embodiment, the base member is from a bending perspective flexible whereby it is capable of extending along a central geometrical axis having various shapes, which is typically required for a biopsy instrument for use in an endoscope. Such a flexible biopsy instrument for use in an endoscope is sometimes referred to as an endoscopic biopsy instrument.

It may be noted that the rotational direction during advancement and retraction may, but need not, be the same. It is e.g. advantageous to have the same rotational direction e.g. in case the base member is stronger in transferring a torque in one rotational direction compared to its capability of transferring a torque in the opposite rotational direction. Such difference in torque transferring capability may e.g. occur in case the base member is designed as a wire, such as a wire rope or a hollow wire rope. In one rotational direction, the windings in the wire has a tendency to tighten and the wire is typically comparably strong when transferring a torque having a tendency to tighten the windings.

Preferred embodiments appear in the dependent claims and in the description.

The smooth inner surface is preferably formed of a polymer based material. The polymer based material may be of a grade commonly referred to as a non-stick polymer. It is advantageous to use a non-stick grade polymer since this reduces the friction between a first tissue sample and the smooth surface and facilitates the transport of the first tissue sample further into the elongated tubular member. Moreover, surfaces that typically are considered non-stick are often smooth enough to provide the desired smoothness. The polymer based material may e.g. be ethylene tetrafluoroethylene, TFE. It is also conceivable to use other plastic materials such as other fluoropolymers. Such fluoropolymers may e.g. be polytetrafluorethylene, PTFE, perfluoroalkoxy, PFA, fluorinated ethylene propylene, FEP.

It may be noted that the polymer based material may be provided in various different physical designs. The polymer based material may be provided in the form of an elongated tubular member. The polymer based material may be attached to an inside of an outer member. The polymer based material may be provided inside an outer member and be movable and rotatable relative to the outer member. The polymer based material may be provided as a coating inside an outer member. The various physical designs will be discussed in more detail below.

The base member is preferably formed of an elongated hollow tube extending from the proximal end to the distal end of the base member. Having the base member being formed of an elongated hollow tube all the way from the proximal end to the distal end facilitates e.g. manufacture since the complete length of the base member may be designed in the same manner. Moreover, it facilitates harvesting since it thereby becomes possible to use a mechanical tool extending through the complete biopsy instrument from the proximal end to the distal end such that the samples may securely be pushed out. An elongated hollow tube also allows for harvesting using a burst of air or injecting fluid at the proximal end pushing the samples out at the distal end. These methods would require that the elongated tube is sufficiently air tight such that a sufficient amount of the burst of air actually pushes the samples out. The elongated hollow tube is preferably designed with a uniform cross-section extending from the proximal end to the distal end; apart from that it is provided with localised irregularities in the form of specific design features at the proximal end as such and/or at the distal end as such. These localised irregularities may e.g. be that the hollow tube is at the proximal end provided with a connector and/or that the hollow tube is at the distal end specifically design to provide a cutting edge or specifically designed to receive a separate member providing said cutting edge.

The base member is preferably from a bending perspective flexible such that the base member is capable of being inserted into and be used together with an endoscope.

The elongated hollow tube comprises preferably an inner elongated hollow tubular member having said smooth interior surface. It may be noted that this inner elongated hollow tubular member may in accordance with one preferred embodiment be fixed relative to an outer elongated hollow tubular member and in accordance with another preferred embodiment be movable relative to an outer elongated hollow tubular member.

The inner elongated hollow tubular member is preferably formed of a polymer based material providing said smooth interior surface. This is a convenient manner of providing a smooth interior surface.

The base member preferably further comprises an outer elongated hollow tubular member.

The inner elongated hollow tubular member is preferably arranged inside the outer elongated hollow tubular member and is in accordance with a first embodiment rotationally and translationally fixed relative to the outer elongated hollow tubular member.

The base member preferably comprises a hollow metallic wire rope capable of transferring a force along the central geometrical axis such that a movement of the proximal end along the central geometrical axis is transferred to a movement of the distal end along the central geometrical axis, and of transferring a torque about the central geometrical axis such that a rotation and a torque applied by a motor at the proximal end about the central geometrical axis is transferred from the proximal end to the distal end thereby rotating the distal end about the central geometrical axis.

The outer elongated hollow tubular member comprises preferably said hollow metallic wire rope. This design is not exclusive to, but is especially useful for, the design in which the inner elongated hollow tubular member is rotationally and translationally fixed relative to the outer elongated hollow tubular member. With this design it is possible to use a relatively standardised component; a hollow metallic wire rope and then provide a basic component of the biopsy instrument by adding an inner elongated hollow tubular member, preferably of a polymer based material, providing the smooth interior surfaces.

The inner elongated hollow tubular member is preferably arranged inside the outer elongated hollow tubular member and is in accordance with a second embodiment rotationally and translationally movable relative to the outer elongated hollow tubular member. One advantage with this design is that the outer elongated hollow tubular member may be kept stationary relative to the endoscope during the sample acquiring process. In this second embodiment it is intended that the inner elongated hollow tubular member is to be advanced into the tissue while the outer elongated hollow tubular member remains outside the tissue. By having a distal end of the outer elongated hollow tubular member being positioned outside the tissue and by advancing the distal end of the inner elongated hollow tubular member into the tissue it facilitates having good control on the insertion depth. The fact that the outer elongated hollow tubular member may be kept stationary relative to the endoscope during the sample acquiring process also making it possible to provide the distal end of the outer elongated hollow tubular member with a stopper preventing the distal end from being unintentionally advanced into the tissue. Moreover, by having an outer elongated hollow tubular member which may be kept stationary relative to the endoscope during the sample acquiring process in combination with an inner elongated hollow tubular member being rotationally and translationally movable relative to the outer elongated hollow tubular member the outer elongated hollow tubular member may be designed with a comparably close fit to the working channel of the endoscope. Moreover, since the relative movement is provided between two components of an instrument being specifically designed and manufactured for interaction with each other, it is possible to provide a comparable close fit between the inner and outer elongated hollow tubular members and still secure that sufficient play is provided. Moreover, by being able to use a close fit, the inner and outer elongated hollow tubular members will in a sense support each other and prevent each other from collapsing, which in turn makes it possible to use comparably thin material thicknesses in both the outer and inner elongated hollow tubular members. This will in turn make it possible to have an inner diameter of the distal end of the inner elongated hollow tubular member being comparably large for a given working channel having a given interior diameter. Other advantages and specific design features made by the second embodiment will be discussed in more detail in the detailed description in relation to the drawings.

Preferably, the rotational movability of the inner elongated hollow tubular member is independent from the translational movability such that the inner elongated hollow tubular member may be rotated by a motor and be moved back and forth independently of the rotational movement.

It may be noted that also in this embodiment—with an inner elongated hollow tubular member being arranged inside the outer elongated hollow tubular member and being rotationally and translationally movable relative to the outer elongated hollow tubular member—the base member may from a bending perspective in accordance with one embodiment be rigid and in accordance with another embodiment be flexible. In the rigid embodiment the base member extends with the central geometrical axis extending along a straight line. Such a rigid biopsy instrument is typically used as a separate biopsy instrument. In such an embodiment the base member may be formed as a needle with a removable inner stylet. The rigid biopsy instrument allows for percutaneous access to a tumour. Typically, in such an embodiment the outer elongated hollow tubular member is fixed and an inner elongated hollow tubular member is rotated by the motorized handle and advanced into tissue after the stylet has been withdrawn. Once the rigid inner stylet has been fully removed the inner hollow tube may be drilled into a hollow space like the abdomen, chest, sinus or joint and used to insert other instruments like cameras, injection devices for fluid or gas or guidewires/rods. In accordance with another embodiment of the embodiment with an inner elongated hollow tubular member being arranged inside the outer elongated hollow tubular member and being rotationally and translationally movable relative to the outer elongated hollow tubular member, the base member is from a bending perspective flexible whereby it is capable of extending along a central geometrical axis having various shapes, which is typically required for a biopsy instrument for use in an endoscope. Such a flexible biopsy instrument for use in an endoscope is sometimes referred to as an endoscopic biopsy instrument.

The flexible inner tube may be used to insert a flexible guide wire and then removed with guide wire in position to be used for insertion of other instruments like stents and dilatation balloons.

The inner elongated hollow tubular member is preferably capable of transferring a force along the central geometrical axis such that a movement of the proximal end along the central geometrical axis is transferred to a movement of the distal end along the central geometrical axis, and of transferring a torque about the central geometrical axis such that a rotation and a torque applied by a motor at the proximal end about the central geometrical axis is transferred from the proximal end to the distal end thereby rotating the distal end about the central geometrical axis.

The inner elongated hollow tubular member has preferably at a proximal end thereof a connector for connection to a motor, the connector being capable of transferring said movement along the central geometrical axis and said rotation and torque.

The inner elongated hollow tubular member is preferably at a distal end thereof provided with said distally facing circular cutting edge.

The above object has also been achieved by a kit of parts comprising a biopsy instrument of the kind disclosed in its basic configuration or in any of the preferred embodiments, and a maneuvering unit comprising a motor, wherein the biopsy instrument is at its proximal end connectable to the motor such that rotation and torque may be applied by the motor to the proximal end of the base member and transferred to the distal end of the base member.

The above object has also been achieved by a method of acquiring a biopsy, the method comprising:

connecting a proximal end of a biopsy instrument to a manoeuvring unit having a motor, moving a distal end of the biopsy instrument to a position where a tissue sample is to be acquired, activating the motor such that rotation is transferred to the distal end of the biopsy instrument, advancing the distal end, which at at least a distal end portion of the base member is shaped as an elongated hollow tube having a distally facing circular cutting edge defining a mouth of the distal end of the hollow tube, into the tissue from which a tissue sample is to be obtained while the distal end is being rotated by the motor thereby cutting a core of the tissue which, due to the advancement of the hollow tube, enters relative to the hollow tube through the mouth into a sample acquiring portion of the hollow tube, retracting the distal end out of the tissue while the distal end is being rotated by the motor with a circumferential outer surface of the core at least partly abutting a smooth interior surface of a hollow elongated tubular sample acquiring portion being provided at a distal portion of the hollow tube, whereby the core of the tissue is detached from the tissue by a pulling force due to the retraction of the hollow tube and due to an adhesive force formed at an interface between the smooth interior surface and the circumferential outer surface of the core which force keeps the core inside the sample acquiring portion having the smooth interior surface.

The above object has also been achieved by a biopsy instrument comprising a base member which extends from a proximal end to a distal end along a central geometrical axis, wherein at least a distal end portion of the base member is shaped as an elongated hollow tube, the distal end being intended to be at least partly inserted into a tissue from which a biopsy is to be obtained, wherein the hollow tube is provided with a distally facing circular cutting edge defining a mouth of the distal end of the hollow tube, wherein the hollow tube has, at a distal portion of the hollow tube, a hollow elongated tubular sample acquiring portion having a smooth interior surface.

It may be noted that it is also conceivable that for some user scenarios, the inner elongated hollow tubular member (rigid or flexible) can be rotated manually at the proximal end resulting in a distally facing circular cutting edge.

BRIEF DESCRIPTION OF THE DRAWINGS

The invention will by way of example be described in more detail with reference to the appended schematic drawings, which shows a presently preferred embodiment of the invention.

FIG. 13a-b discloses a first and a second position of the distal end of the biopsy instrument while acquiring a tissue sample along a surface of the tissue.

FIG. 14a discloses the distal end of the biopsy instrument while acquiring a tissue sample along a surface of the tissue as seen in a cross-sectional view of FIGS. 13a-b.

FIG. 14b discloses the tissue having a groove in the surface being formed by the biopsy instrument as shown in FIGS. 13a-b and 14a.

FIG. 14c is a top-plan view of the tissue and the groove of FIG. 14b.

FIG. 22 discloses a motor, a telescope functionality and a biopsy instrument and discloses schematically an example of an interface of the biopsy instrument being configured to be connected to the telescope functionality.

FIG. 23 discloses an outer rigid hollow needle and an inner rigid hollow needle configured to be positioned inside the outer rigid hollow needle.

FIG. 24 discloses the inner rigid hollow needle being inserted into the rigid outer hollow needle.

FIG. 25 discloses the inner rigid hollow needle and the outer rigid hollow needle in a retracted position of the inner rigid hollow needle in which position the needles are configured to be handled and to be inserted into a handle for operation in the sample acquiring method.

DETAILED DESCRIPTION OF PREFERRED EMBODIMENTS

Figure 1:
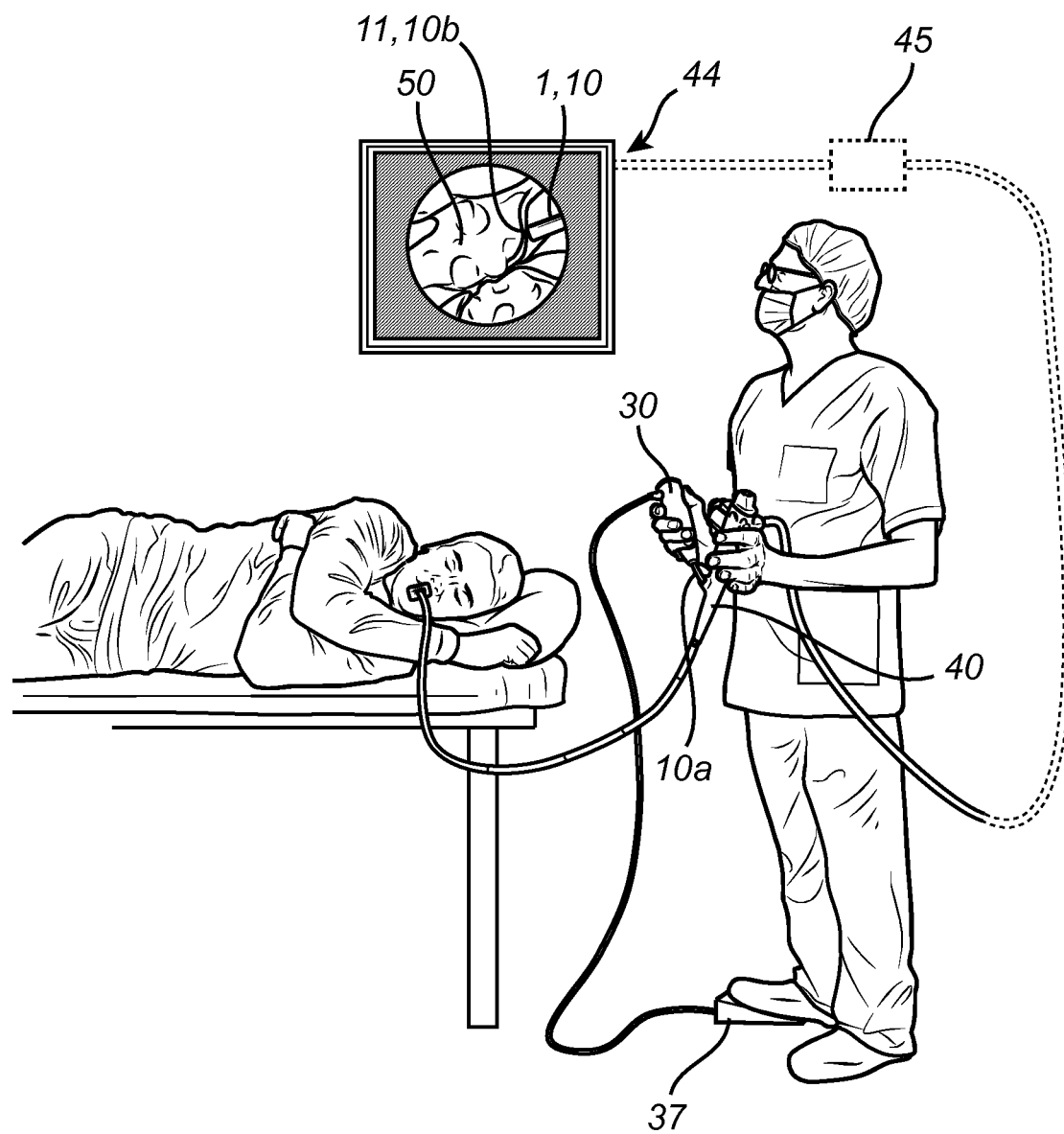
FIG. 1 discloses schematically a physician using a biopsy instrument and an endoscope to obtain a tissue sample from a patient.
Figure 2:
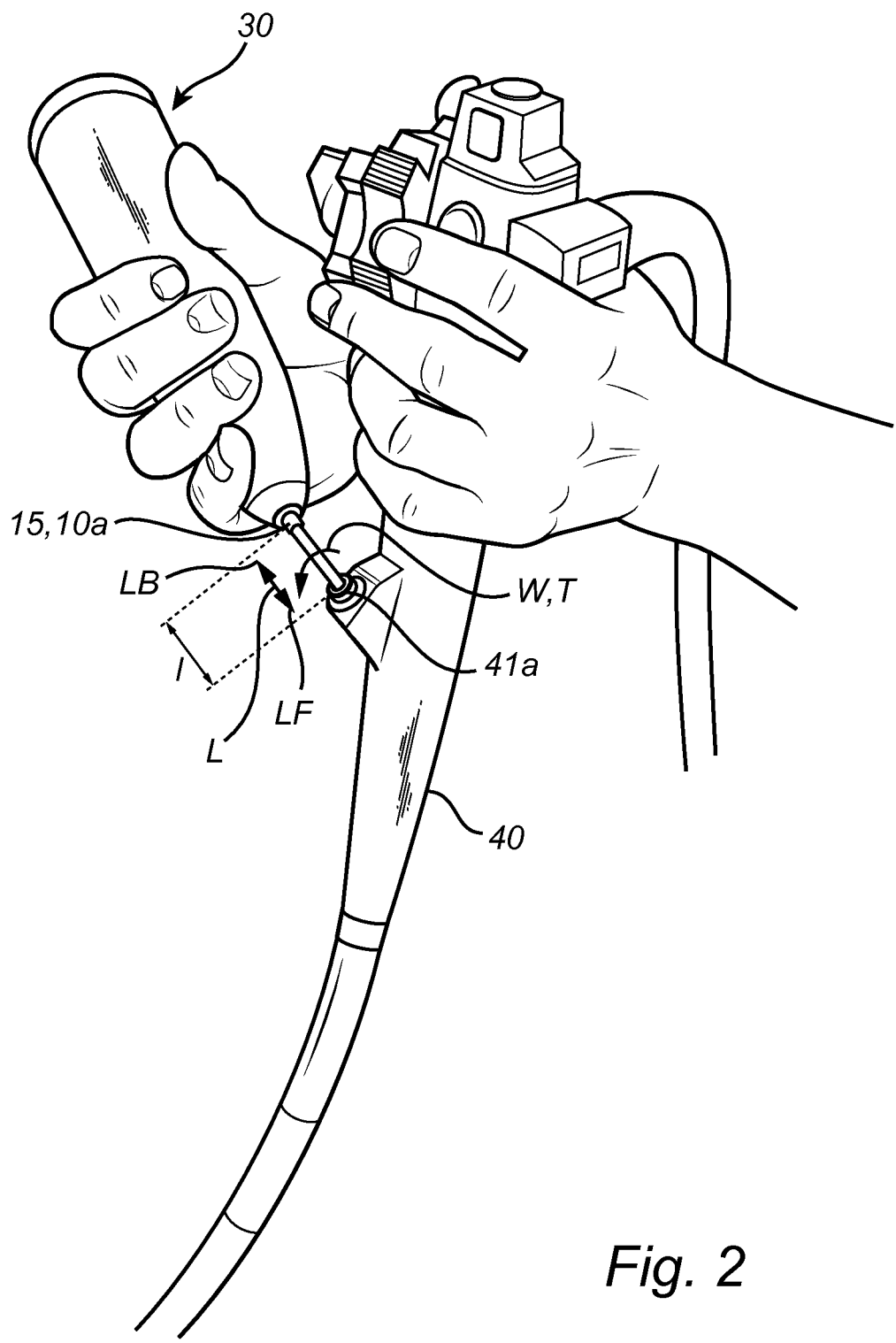
FIG. 2 discloses in more detail the proximal end of the endoscope and the proximal end of the biopsy instrument.

In FIG. 1, there is generally disclosed a how a user U, such as a physician, uses an endoscope 40 to guide a biopsy instrument 1 to a sample site 50 through a body cavity of a patient P. The biopsy instrument 1 is inserted into the patient's body to the intended sample site 50 by the endoscope 40 being inserted through a body cavity of the patient and with the biopsy instrument 1 being inserted in a working channel 41 of the endoscope 40. As shown in FIG. 1 and in more detail in FIG. 2, the endoscope is provided with an access opening 41a at the proximal end of the remaining outside of the patient's body, wherein the biopsy instrument 1 is intended to be inserted into the endoscope via the access opening 41a. The endoscope 40 is typically provided with a camera and/or an ultrasound probe and is typically connected to a screen 44 via a processing unit 45 capable of transform the data from the camera or ultrasound probe into an image on the screen 44.

Figure 11:
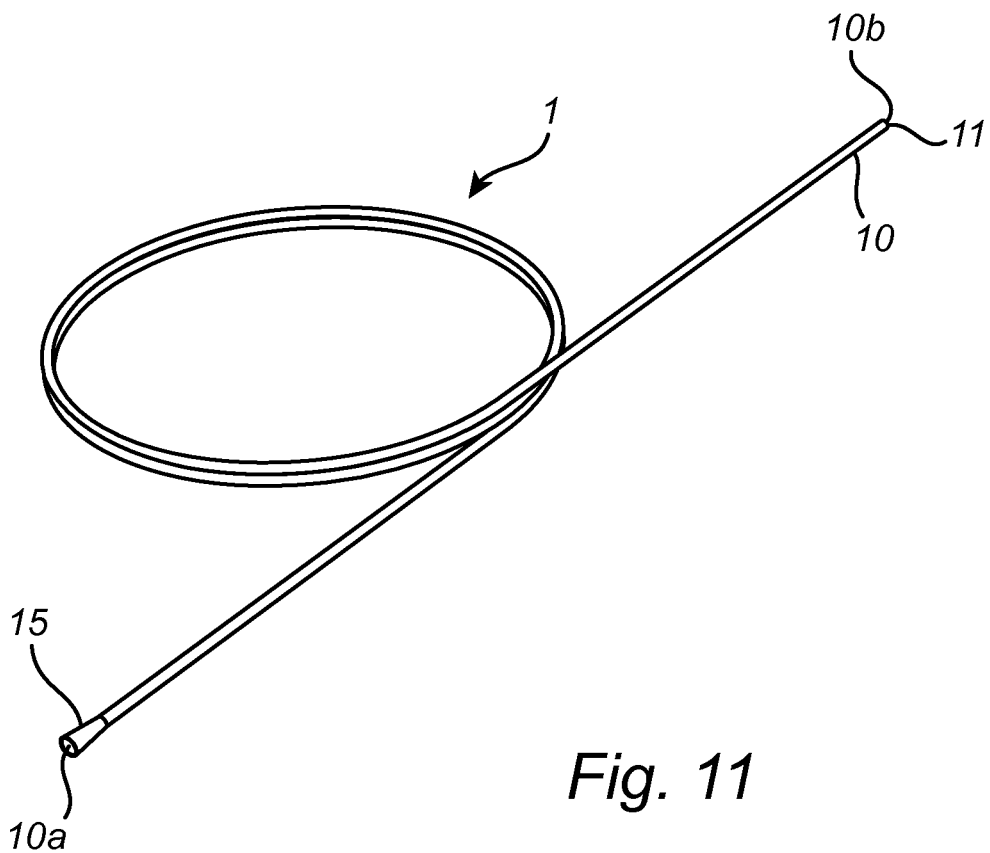
FIG. 11 discloses a flexible biopsy instrument.

The biopsy instrument 1 comprises a base member 10 which extends from a proximal end 10a to a distal end 10b along a central geometrical axis A. One embodiment of the complete biopsy instrument 1 is shown in FIG. 11. In the embodiment shown in FIG. 11, the base member 10 is from a bending perspective flexible. It is thereby capable of extending along a central geometrical axis A having various shapes, which is typically required for a biopsy instrument 10 for use in an endoscope 40. Such a flexible biopsy instrument 1 for use in an endoscope 40 is sometimes referred to as an endoscopic biopsy instrument 1. However, it may be noted that the biopsy instrument 1 is also useful for applications where it is not used in an endoscope. In such an instance it may, from a bending perspective, be rigid and extend with the central geometrical axis A extending along a straight line. Such a rigid biopsy instrument is typically used as a separate biopsy instrument 1. The proximal end 10a is shown in its context in FIGS. 1 and 2 and the distal end 10b is shown in its context e.g. in FIGS. 3 and 4.

Figure 3:
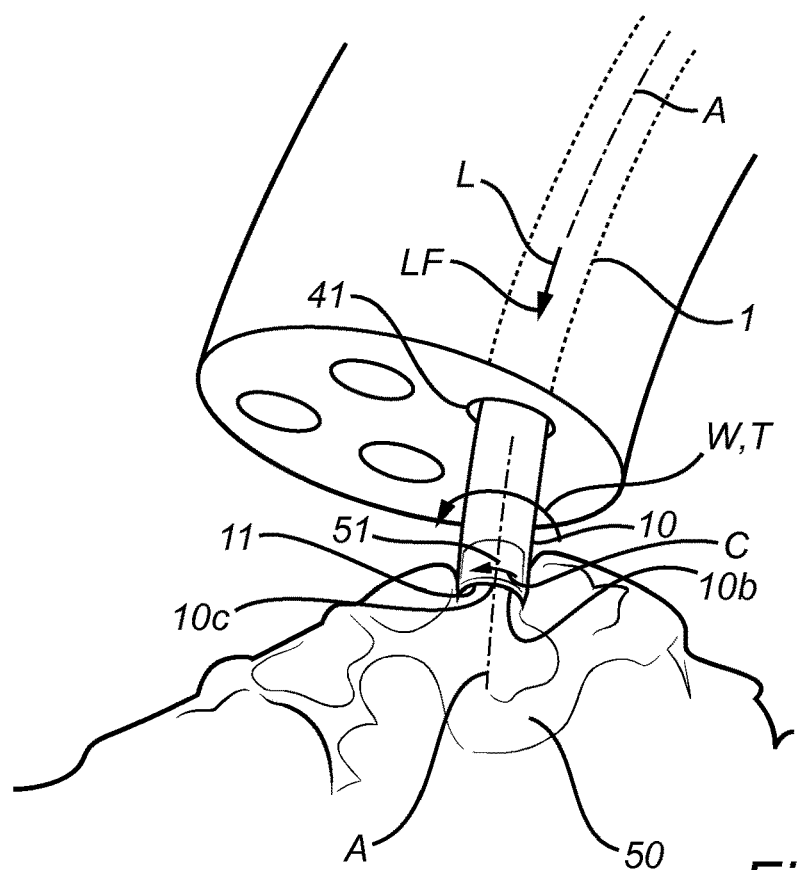
FIG. 3 discloses the distal end of the endoscope and the distal end of the biopsy instrument being advanced into the tissue from which a sample is to be acquired.
Figure 4:
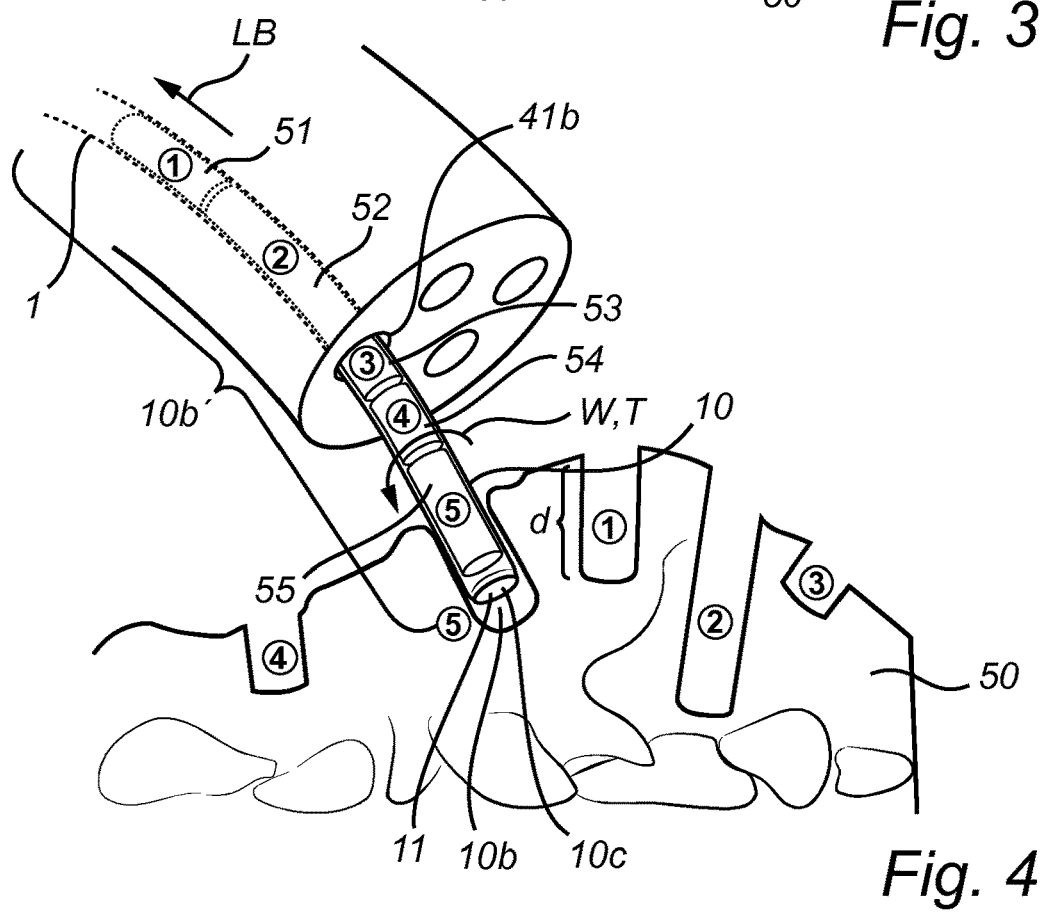
FIG. 4 discloses the endoscope and instrument shown in FIG. 3 after several samples has been acquired.

As is shown e.g. in FIGS. 3 and 4, at least a distal end portion 10b' of the base member 10 is shaped as an elongated hollow tube 10. In the preferred embodiments shown in detail in FIGS. 12 and 15-16, respectively, the base member 10 is shaped as a hollow tube 10 extending from the proximal end 10a to the distal end 10b of the base member 10.

As is shown in FIGS. 3 and 4, the distal end 10b, being shaped as an elongated hollow tube 10, is intended to be at least partly inserted into a tissue 50 from which a biopsy is to be obtained. In the user case shown in FIGS. 3 and 4, the distal end 10b is fully inserted into the tissue in the sense that the distal end 10b is inserted with the complete circumference C inserted into the tissue 50. In the user case shown in FIGS. 13a-b and 14a-c, the distal end 10b is only partly inserted into the tissue in the sense that the distal end 10b is inserted with only a portion of the complete circumference C being inserted into the tissue 50.

The base member 10 is capable of transferring a force along the central geometrical axis A such that a movement LF, LB of the proximal end 10a along the central geometrical axis A is transferred to a movement LF, LB of the distal end 10b along the central geometrical axis A. The base member 10 is also capable of transferring a torque about the central geometrical axis A such that a rotation ω and a torque T applied by a motor 31 at the proximal end 10a about the central geometrical axis A is transferred from the proximal end 10a to the distal end 10b thereby rotating the distal end 10b about the central geometrical axis A. The distal end 10b of the base member 10 is thereby manoeuvrable by advancing and retracting the proximal end 10a and by applying a rotation ω and a torque T at the proximal end 10a.

The biopsy instrument 1 is intended to be used in accordance with the brief disclosure presented above with reference to FIG. 1. The intended method of use will in the following be disclosed in more detail with reference to FIGS. 1 and 2. The user U has connected a proximal end 10a of a biopsy instrument 10 to a manoeuvring unit 30 having a motor 31. By moving the endoscope 40 and then by moving a distal end 10b of the biopsy instrument 1 relative to the endoscope 40, the distal end 10b of the biopsy instrument 1 is moved to a position where a tissue sample is to be acquired. The user U is in this movement guided by the image on the screen 44. Thereafter, the user U activates the motor 31 such that rotation is transferred to the distal end 10b of the biopsy instrument 1. Thereafter, the user U advances the distal end 10b, which at at least a distal end portion 10b' of the base member 10 is shaped as an elongated hollow tube 10 having a distally facing circular cutting edge 11 defining a mouth 10c of the distal end 10b of the hollow tube 10, into the tissue 50 from which a tissue sample is to be obtained while the distal end 10b is being rotated by the motor 31 thereby cutting a core 51 of the tissue 50 which, due to the advancement LF of the hollow tube 10, enters relative to the hollow tube 10 through the mouth 10c into a sample acquiring portion 10b' of the hollow tube 10. This advancement may be said to be that the biopsy instrument 10 is moved relative to the endoscope 40 in a direction extending from the proximal end 10a to the distal end 10b. This advancement is, in the embodiment of FIG. 2, performed by moving the manoeuvring unit 30 forward along the arrow LF relative to the endoscope 40 and the access opening 41a, such that the free distance I of the biopsy instrument 10 decreases. Once the distal end 10b has been inserted into the tissue 50 to the intended depth d, the user U thereafter retracts the distal end 10b out of the tissue 50 while the distal end 10b is being rotated by the motor 31 with a circumferential outer surface of the core 51 at least partly abutting a smooth interior surface 12 of a hollow elongated tubular sample acquiring portion 10b' being provided at a distal portion 10b' of the hollow tube 10, whereby the core 51 of the tissue 50 is detached from the tissue 50 by a pulling force due to the retraction LB of the hollow tube 10 and due to an adhesive force formed at an interface between the smooth interior surface 12 and the circumferential outer surface of the core 51 which force keeps the core 51 inside the sample acquiring portion 10b' having the smooth interior surface 12.

Figure 12:
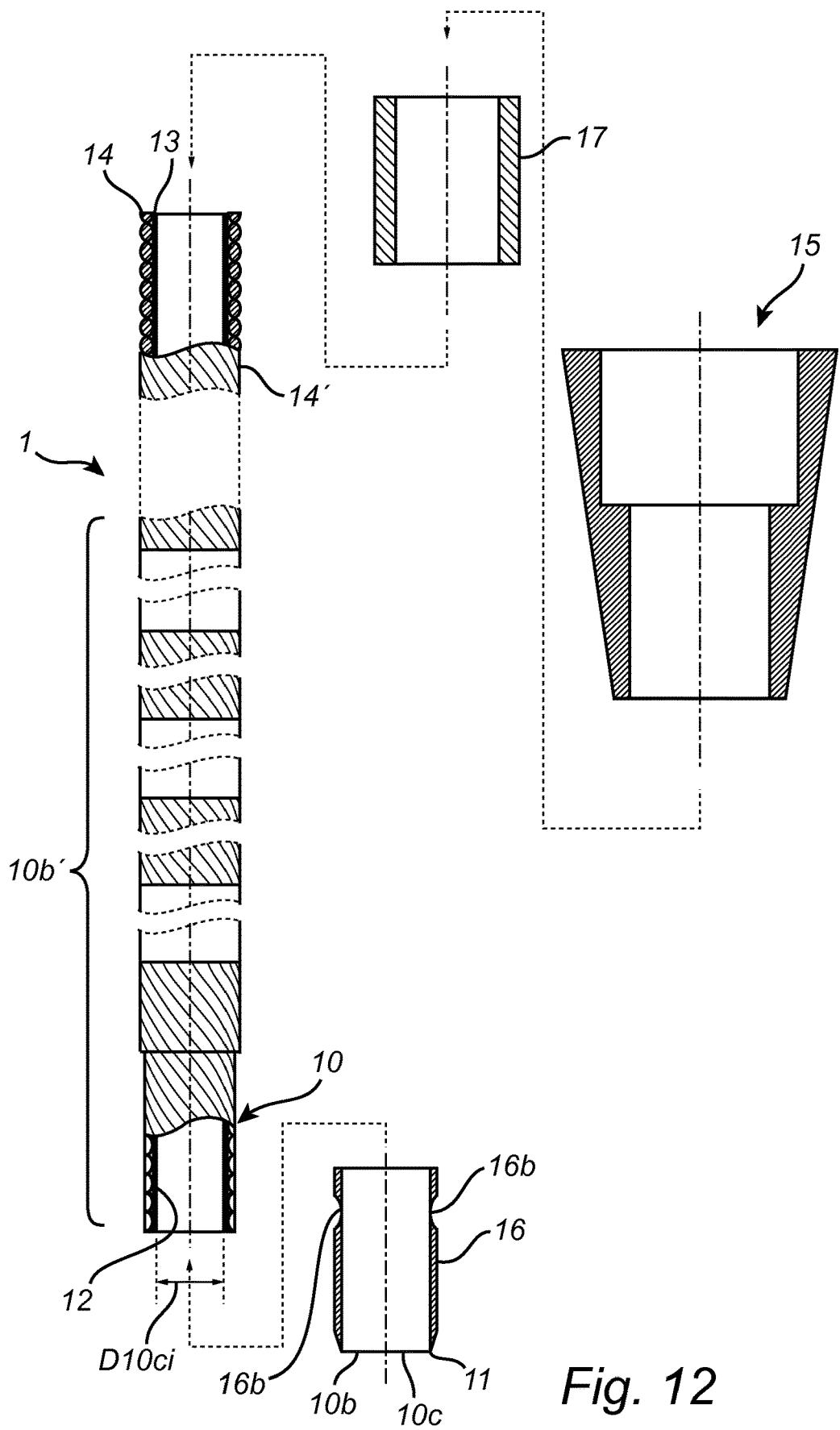
FIG. 12 the flexible biopsy instrument in more detail in a cross-sectional and exploded view.
Figure 16:
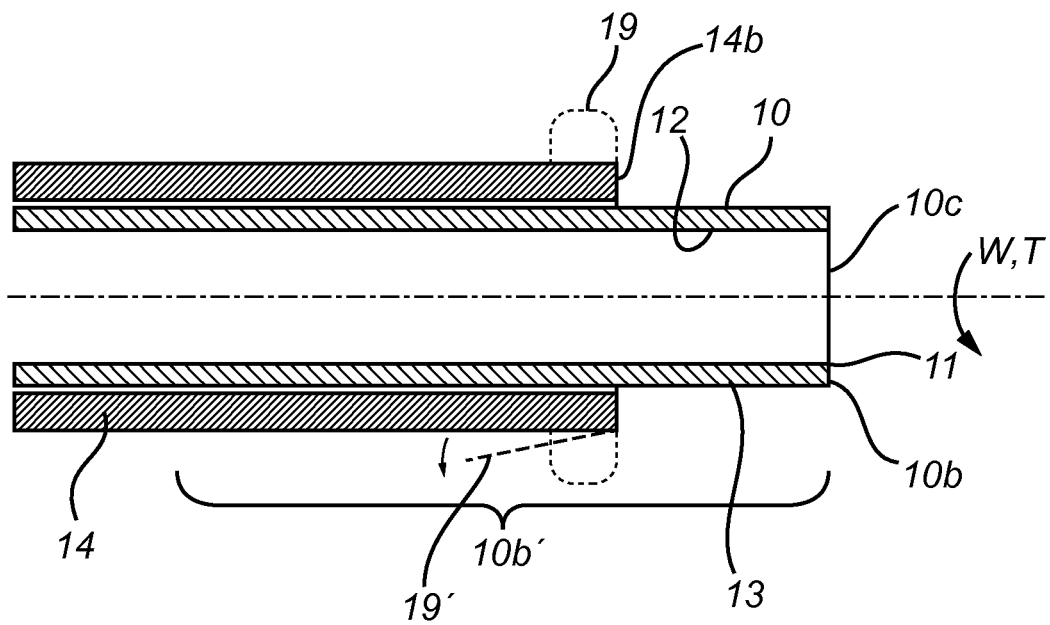
FIG. 16 is another cross-sectional view of the biopsy instrument of FIG. 15.

As is e.g. schematically shown in FIGS. 3 and 4 and is shown in more detail in FIGS. 12 and 16, the hollow tube 10 is provided with a distally facing circular cutting edge 11 defining a mouth 10c of the distal end 10b of the hollow tube 10. In the preferred embodiments, the distally facing circular cutting edge 11 has, as seen along the circumference C of the mouth 11c a straight-line configuration. It is also preferred that the mouth 11c defines a plane having a normal parallel to the extension of the central geometrical axis A as the central geometrical axis passes through said plane of the mouth 11c. That is, the hollow tube 10 is in the most preferred embodiment cut by a plane orthogonal to the longitudinal extension of the hollow tube 10 at the mouth 11c.

The hollow tube 10 has, at a distal portion 10b' of the hollow tube 10, a hollow elongated tubular sample acquiring portion 10b' having a smooth interior surface 12. The tubular sample acquiring portion 10b' has a length along the central geometrical axis A, the length preferably being sufficient to allow a plurality of samples 51, 52, 53, 54, 55 to be collected and positioned one after the other in the tubular sample acquiring portion 10b' along the central geometrical axis A. The length is preferably at least 10 times, and more preferably at least 20 times, the inner diameter $D11ci$ of the hollow tube 10. However, as mentioned above, the base member 10 is preferably formed of the elongated hollow tube 10 extending from the proximal end 10a to the distal end 10b of the base member 10. Thereby it may be said that the hollow elongated tubular sample acquiring portion 10b' is basically formed all the way from the distal end 10b to the proximal end 10a.

The elongated hollow tube 10 is preferably designed with a uniform cross-section extending from the proximal end 10a to the distal end 10b; apart from that it is provided with localised irregularities in the form of specific design features at the proximal end 10a as such and/or at the distal end 10b as such. These localised irregularities may e.g. be that the hollow tube 10 is at the proximal end 10a provided with a connector 15 and/or that the hollow tube 10 is at the distal end 10b specifically design to provide a cutting edge 11 or specifically designed to receive a separate member providing said cutting edge 11.

The smooth interior surface 12 is smooth to such an extent that when a reference biopsy is to be acquired in accordance with is shown in FIGS. 3 and 4, the cutting edge 11 and the distal end 10b of the hollow tube 10 is configured to be advanced along the central geometrical axis A into a tissue 50 while being rotated ω, T by being motor driven at its proximal end 10a and thereby cutting a core 51 of the tissue 50 which, due to the advancement LF of the hollow tube 10, enters relative to the hollow tube 10 through the mouth 10c into the sample acquiring portion 10b' of the hollow tube 10 with a circumferential outer surface of the core 51 at least partly abutting the smooth interior surface 12 of the sample acquiring portion 10b', where-after the hollow tube 10 is retracted from the tissue 50 while being rotated ω, T by being motor driven at its proximal end 10a whereby the core 51 of the tissue 50 is detached from the tissue 50 by a pulling force due to the retraction LB of the hollow tube 10 and due to an adhesive force formed at an interface between the smooth interior surface 12 and the circumferential outer surface of the core 51 which force keeps the core 51 inside the sample acquiring portion 10b' having the smooth interior surface 12. The surface 12 is preferably smooth to such an extent that when performing a reference sample with a biopsy instrument 1 of the above kind, a core 51 is, during retraction of the hollow tube 10, detached from the tissue 50 in case the distal end 10b has been inserted into the tissue 50 a distance being the same or greater than an inner diameter $D10ci$ of the mouth 10c. However, it is in many cases acceptable that the surface 12 is smooth to such an extent that when performing a reference sample with a biopsy instrument 1 of the above kind, a core 51 is, during retraction of the hollow tube 10, detached from the tissue 50 in case the distal end 10b has been inserted into the tissue 50 a distance being 1,3 times or greater than an inner diameter $D10ci$ of the mouth 10c. Moreover, it is in many cases acceptable that the surface 12 is smooth to such an extent that when performing a reference sample with a biopsy instrument 1 of the above kind, a core 51 is, during retraction of the hollow tube 10, detached from the tissue 50 in case the distal end 10b has been inserted into the tissue 50 a distance being 1,7 times or greater, or even 2 times or greater, than an inner diameter D10ci of the mouth 10c. The above applies at least for inner diameters D10ci being between 1-5 mm.

It may be noted that the smallest or most superficial sample that typically may be obtained typically depends on the type of tissue and tumour being sampled. In general, more solid tissue and tumours are easier to sample and biopsies of down to 1 mm are typically possible. In mucosa it also depends on which organs the biopsy is retrieved from since the consistency also varies e.g. a comparably softer gastrointestinal vs a comparably more solid respiratory tract. Biopsies between 1-3 mm may typically be obtained in most types of tissues and tumours with high reproducibility.

As is shown in FIG. 4, the biopsy instrument 1 is capable of retrieving a plurality of tissue samples directly one after the other without a previous sample needs to be harvested. A first sample 51 is in a controlled manner pushed further into the hollow tube 10 towards the proximal end 10a by the core 52 of the second sample when the distal end 10b is advanced into the tissue 50. The fact that the hollow tube 10 is provided with a smooth interior surface 12 being smooth to such an extent that the core 51 adhesively by itself becomes adhered to the inside of the hollow tube 10 makes it possible to retrieve samples with a minimum of damage to the sample 51 and still allow for the cutting edge 11 and distal end 10b to be drilled into and out of the tissue 50 thereby reducing discomfort for the patient.

The hollow tube 10 is air tight. However, it should be noted that the air tightness is not intended to address any long term air or gas tightness which is typically discussed when it comes to long term storing of a gas. The hollow tube 10 should be air tight such that suction is provided at the interface between the inside wall of the hollow tube 10 and the core 51 of the tissue sample when the hollow tube 10 is retracted. The hollow tube 10 is air-tight at least along the length of the tubular sample acquiring portion 10b' along the central geometrical axis A. The tubular sample acquiring portion 10b' has preferably an extension and is provided with said smooth surfaces 12 along a length 10b' from the distal end 10b towards the proximal end 10a, the extension 10b' having at least a length allowing for at least two, preferably at least three, reference samples of the above disclosed kind each having an insertion depth being at least equal to, or at least 1,3 times, or at least 1,7, or even 2 times the inner diameter D10ci to be acquired one after the other. In the preferred embodiment, the hollow tube 10 is air tight along the complete length from the proximal end 10a to the distal end 10b.

Figure 6:
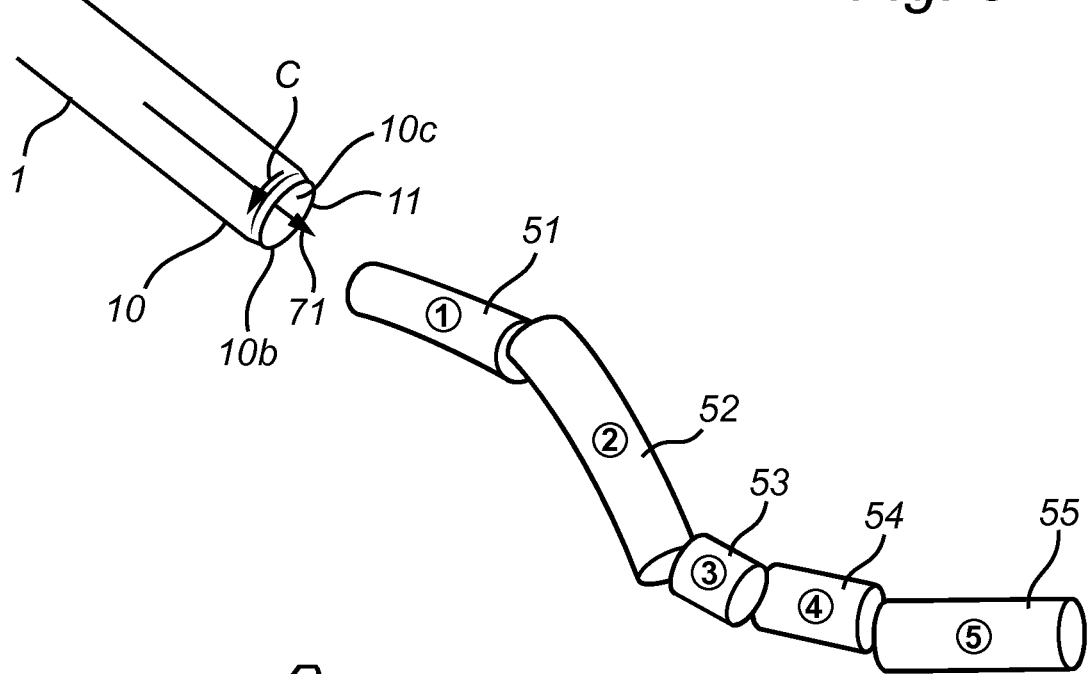
FIG. 6 discloses harvesting of the samples from the biopsy instrument.

As is shown in FIG. 6, the samples 51, 52, 53, 54, 55 may be harvested in a controlled manner such that each sample 51, 52, 53, 54, 55 is still uniquely identifiable and still undamaged. This allows for the physician to keep any information provided by the stratigraphy and/or position of respective sample 51, 52, 53, 54, 55, which in turn may be used to increase the amount of data provided by the biopsy, which in turn may increase the accuracy of the diagnosis ultimately provided.

Figure 7:
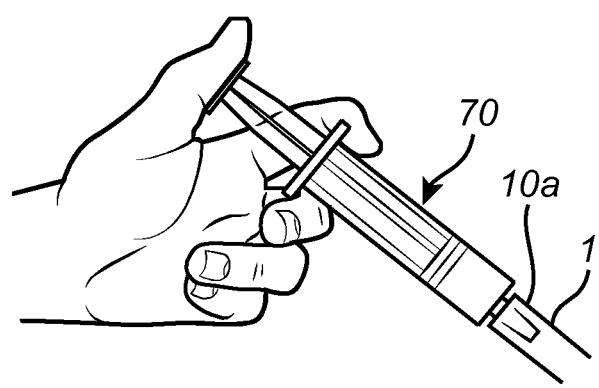
FIG. 7 discloses harvesting using an overpressure provided by a syringe.

Harvesting may e.g. be performed by using a mechanical tool schematically indicated by the arrow 71 in FIG. 6 being inserted into and extending through the complete biopsy instrument from the proximal end 10a to the distal end 10b such that the samples 51, 52, 53, 54, 55 may securely be pushed out. As is shown in FIG. 7, an elongated hollow tube 10 also allows for harvesting using a burst of air at the proximal end 10a pushing the samples 51, 52, 53, 54, 55 out at the distal end 10b. This latter would require that the elongated tube 10 is sufficiently air tight such that a sufficient amount of the burst of air, or other kinds of gaseous or liquid fluids, actually pushes the samples 51, 52, 53, 54, 55 out. The burst of air may e.g. be provided by a syringe 70 being connected to the proximal end 10a of the hollow tube 10.

The smooth inner surface 12 is preferably formed of a polymer based material 12. The polymer based material may e.g. be ethylene tetrafluoroethylene ETFE. It is also conceivable to use other plastic materials such as other fluoropolymers, such as polytetrafluorethylene PTFE, perfluoroalkoxy PFA, fluorinated ethylene propylene FEP.

It may be noted that the polymer based material 12 may be provided in various different physical designs. The polymer based material 12 may be provided in the form of an elongated tubular member. The polymer based material 12 may be attached to an inside of an outer member. The polymer based material 12 may be provided inside an outer member and be movable and rotatable relative to the outer member. The polymer based material 12 may be provided as a coating inside an outer member. The various physical designs will be discussed in more detail below.

Common to both detailed embodiments is that the elongated hollow tube 10 comprises an inner elongated hollow tubular member 13 having said smooth interior surface 12. It may be noted that this inner elongated hollow tubular member 13 is in accordance with one preferred embodiment fixed relative to an outer elongated hollow tubular member 14 and in accordance with another preferred embodiment is movable relative to an outer elongated hollow tubular member 14. In both detailed embodiments, the inner elongated hollow tubular member 13 is formed of a polymer based material providing said smooth interior surface 12.

In the embodiment shown in detail in FIG. 11, the inner elongated hollow tubular member 13 is arranged inside the outer elongated hollow tubular member 14 and is rotationally and translationally fixed relative to the outer elongated hollow tubular member 14.

As is shown in FIG. 12, the outer elongated hollow tubular member 14 comprises a hollow metallic wire rope capable of transferring a force along the central geometrical axis A such that a movement LF, LB of the proximal end 10a along the central geometrical axis A is transferred to a movement LF, LB of the distal end 10b along the central geometrical axis A, and of transferring a torque about the central geometrical axis A such that a rotation ω and a torque T applied by a motor 31 at the proximal end 10a about the central geometrical axis A is transferred from the proximal end 10a to the distal end 10b thereby rotating the distal end 10b about the central geometrical axis A.

As is e.g. shown in FIGS. 11 and 12, the hollow tube 10 has at a proximal end 13a thereof a connector 15 for connection to a motor 31, the connector 15 being capable of transferring said movement LF, LB along the central geometrical axis A and said rotation ω and torque T.

The hollow tube 10 further comprises an outside layer 14' arranged outside of outer elongated hollow tubular member 14. The outside layer 14' may e.g. be a polymer based shrink film.

As is indicated in FIG. 12, the hollow tube 10 is in accordance with a first embodiment designed and optionally also manufactured in accordance with the following.

A hypotube 16 is mounted to the proximal end 10b of the hollow metallic wire rope 14, which proximal end 10b has been ground. The hyoptube 16 is provided with a sharpened cutting edge 11. The hypotube 16 also has openings 16b used in a laser welding process by which the hypotube 16 is fastened to the outside of the hollow metallic wire rope 14. A base connector 17 is crimped or shrunk onto the proximal end 10*a* of the hollow metallic wire rope 14. The base connector 17 is in turn designed to be connected to a connector 15, wherein the connector 15 is designed to be connected to a manoeuvring unit 30. In a sense it may be said that the base connector 17 forms part of the connector 15. The connector 15, 17 is manufactured in two main parts 15, 17 since it is advantageous to have a small and straightforward design on the part 17 actually being attached to the hollow metallic wire rope 14. The desired functionality concerning user friendly connectivity between the connector 15 and the manoeuvring unit 30 is then provided by the connector 15. The connection between the base connector 17 and the connector 15 is such that it is capable of transferring said force along the central geometrical axis A and of transferring said torque about the central geometrical axis A such that said rotation ω and said torque T may be transferred.

The inner elongated hollow tubular member 13 is positioned inside the hollow metallic wire rope 14. The inner elongated hollow tubular member 13 is welded to the hollow metallic wire rope 14. The inner elongated hollow tubular member 13 preferably has an over-length compared to the length of the hollow metallic wire rope 14 when it is positioned inside the hollow metallic wire rope 14 and is welded and fixated in its position before it is cut in flush. It may also be mentioned that it is preferred that the cutting edge 11*c* also is flush with the distal end 10*a* of the hollow tube 10. Thereby will the smooth surface 12 extend all the way up to the distal end 10*a*.

An outer shrink tube 14' is shrunk onto the outside of the hollow metallic wire rope 14.

Figure 15:
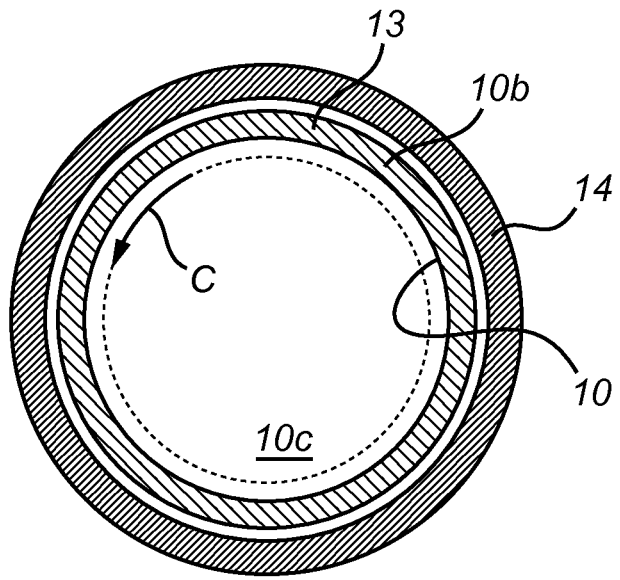
FIG. 15 is a cross-sectional view of a biopsy instrument in accordance with a second embodiment.

With reference to FIGS. 15 and 16, an embodiment in which the inner elongated hollow tubular member 13 is arranged inside the outer elongated hollow tubular member 14 and is rotationally and translationally movable relative to the outer elongated hollow tubular member 14 will be described in more detail in the following. The outer elongated hollow tubular member 14 is intended to be kept stationary relative to the endoscope during the sample acquiring process. The inner elongated hollow tubular member 13 is intended to be rotated and to be advanced into the tissue 50 while the outer elongated hollow tubular member 14 remains outside the tissue 50. The distal end 14*b* of the outer elongated hollow tubular member 14 is provided with a stopper 19 as is shown in FIG. 16, The stopper 19 prevents the distal end 14*b* from being unintentionally advanced into the tissue 50. The stopper 19 is designed to increase the abutment surface between the distal end 14*b* of the outer elongated hollow tubular member 14 and the tissue 50. The stopper 19 provides this increased abutment surface by being positioned at the distal end 14*b* and by being designed to provide one or more bodies increasing the circumference of the distal end 14*b*. The stopper 19 may be an inflatable ring 19 attached to the outer elongated hollow tubular member 14. The stopper 19 may be one or more arms 19' pivotably connected to the outer elongated hollow tubular member 14. The increased abutment surface provided by stopper 19 leads to stability and works as an opposing force when the inner elongated hollow tubular member 13 is retracted whereby the sample may be removed more easily and without as much pull on the tissue surrounding the sample site. Moreover, by having an outer elongated hollow tubular member 14 which may be kept stationary relative to the endoscope during the sample acquiring process in combination with an inner elongated hollow tubular member 13 being rotationally and translationally movable relative to the outer elongated hollow tubular member 14 the outer elongated hollow tubular member 14 may be designed with a comparably close fit to the working channel 41 of the endoscope. Moreover, since the relative movement is provided between two components of an instrument being specifically designed and manufactured for interaction with each other, it is possible to provide a comparable close fit between the inner and outer elongated hollow tubular members 13, 14 and still secure that sufficient play is provided. Moreover, by being able to use a close fit, the inner and outer elongated hollow tubular members 13, 14 will in a sense support each other and prevent each other from collapsing, which in turn makes it possible to use comparably thin material thicknesses in both the outer and inner elongated hollow tubular members 13, 14. This will in turn make it possible to have an inner diameter D10*ci* of the distal end 13*b* of the inner elongated hollow tubular member 13 being comparably large for a given working channel 41 having a given interior diameter. Other advantages and specific design features made by the second embodiment will be discussed in more detail in the detailed description in relation to the drawings.

The inner elongated hollow tubular member 13 is capable of transferring a force along the central geometrical axis A such that a movement LF, LB of the proximal end 10*a* along the central geometrical axis A is transferred to a movement LF, LB of the distal end 10*b* along the central geometrical axis A, and of transferring a torque about the central geometrical axis A such that a rotation ω and a torque T applied by a motor 31 at the proximal end 10*a* about the central geometrical axis A is transferred from the proximal end 10*a* to the distal end 10*b* thereby rotating the distal end 10*b* about the central geometrical axis A.

The inner elongated hollow tubular member 13 has at a proximal end 13*a* thereof a connector 15 for connection to a motor 31, the connector 15 being capable of transferring said movement LF, LB along the central geometrical axis A and said rotation ω and torque T.

The outer elongated hollow tubular member 14 has at a proximal end 13*a* thereof a connector 18 for connection to a manoeuvring unit 30 such that the outer elongated hollow tubular member 14 may be moved to the intended sample site and be kept still during the sample being acquired by the advancement LF and retraction LB of the inner elongated hollow tubular member 13 while the inner elongated hollow tubular member 13 being rotated by the motor 31.

The inner elongated hollow tubular member 13 is at the distal end thereof provided with said distally facing circular cutting edge 11. The cutting edge 11 may be provided on a separate member such as a hypotube similar to the hypotube 16. However, since the inner and outer elongated hollow tubular members 13, 14 support each other and thereby may be designed with thin material thicknesses it is conceivable to use a cut distal end of the inner elongated hollow tubular member 13 as such as the cutting edge 11.

Figure 8:
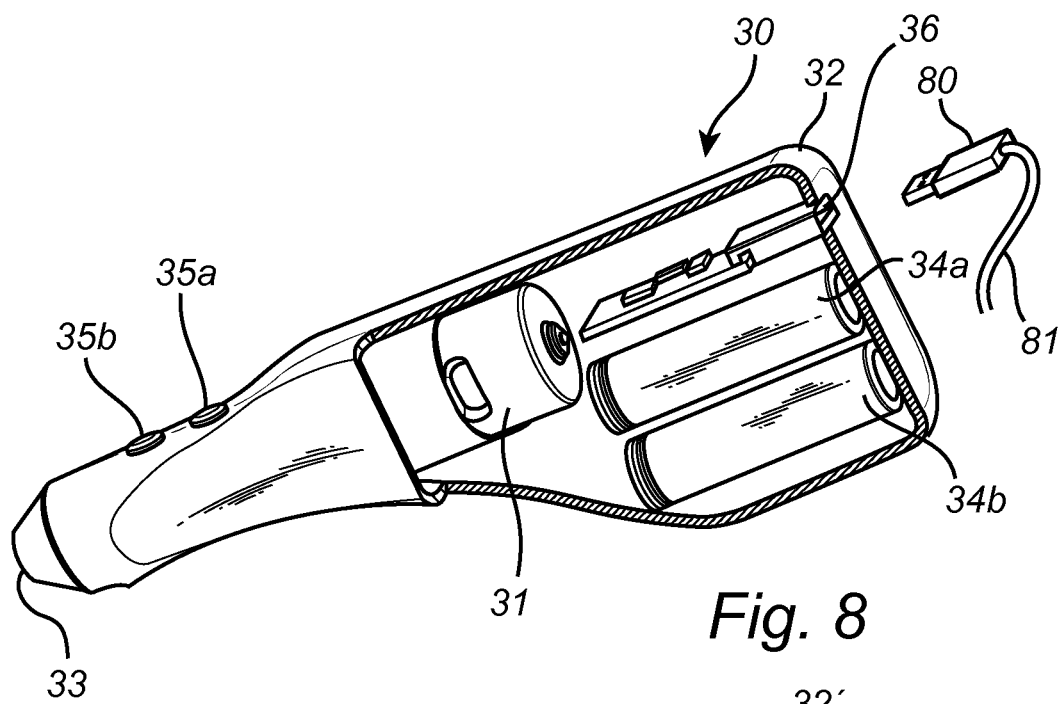
FIG. 8 discloses an inside of a manoeuvring member configured to be attached to the proximal end of the biopsy instrument.
Figure 9:
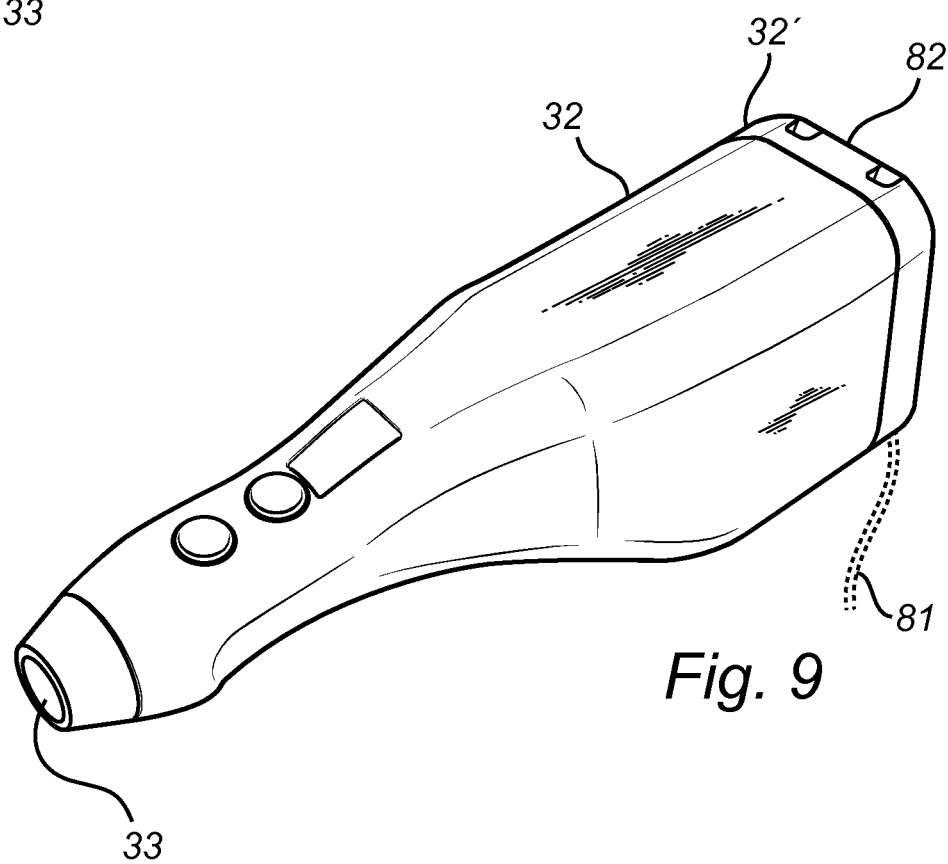
FIG. 9 discloses the outside and manoeuvring buttons of the manoeuvring member of FIG. 8.
Figure 10:
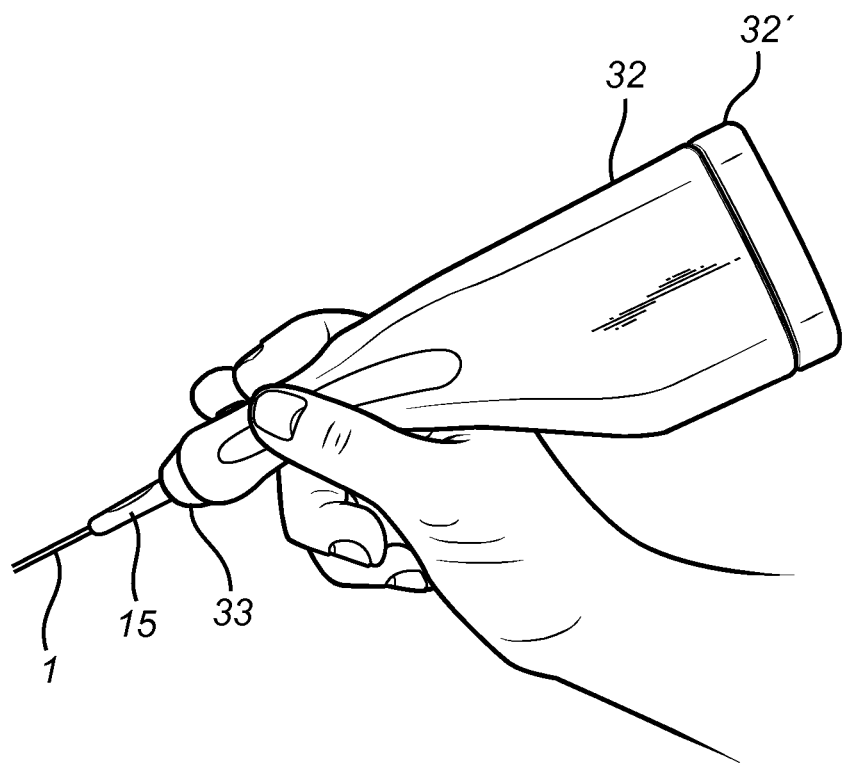
FIG. 10 discloses the manoeuvring member being attached to the proximal end of the biopsy instrument.

The manoeuvring unit 30 comprises in short a housing 32, an electric motor 31 inside the housing 32, and a connector 33. The connector 33 is configured to be interconnected with the connector 15 and is connected to the motor 31 such that a torque T and rotation ω may be transferred from the motor 31 to the connector 15. The manoeuvring unit 30 also comprises one or more batteries 34*a-b*. The manoeuvring unit 30 may be provided with one or more buttons 35*a-b*. The buttons 35*a-b* may e.g. be used start and stop the motor 31. The manoeuvring unit 30 may be provided with one or more connections as exemplified by connection 36. The connection 36 may e.g. be used to provide an interface to a pedal 37, which is shown in FIG. 1, whereby the pedal 37 may be used to start and stop the motor 31. The user U may e.g. be given the option to vary the rotational speed by depressing/releasing the pedal 37. A connection 36 may also be used for charging the batteries 34a-b in the manoeuvring unit 30. The connection 36 and housing 32 may be configured to receive a connector 80 extending from the connection 36 as a typical connector 80 at an end of an electrical wire 81 as shown in FIG. 8. The connection 36 and housing 32 may be configured to receive a sub-housing 82 having a shape and size forming an extended part 32' of the housing 32. It may e.g. have the same circumferential shape and size and be attached to the end of the housing 32 as shown in FIGS. 9 and 10. An electric wire 81 may extend from this part 32' of the housing 32. Such an extended part 32' of the housing 32 may house the batteries 34a-b. The batteries 34a-b may thereby be quickly replaceable, they may be charged separated from the housing part comprising the motor 31 and connector 33, and it is possible to use a single manoeuvring unit 30 with the motor 31 and connector 33 together with more than one extended parts 32 each being provided with an own set of said one or more batteries 34a-b.

In FIG. 10, it is shown how the manoeuvring unit 30 is connected to the biopsy instrument 1 by the connector 15 being connected to the connector 33.

Figure 17:
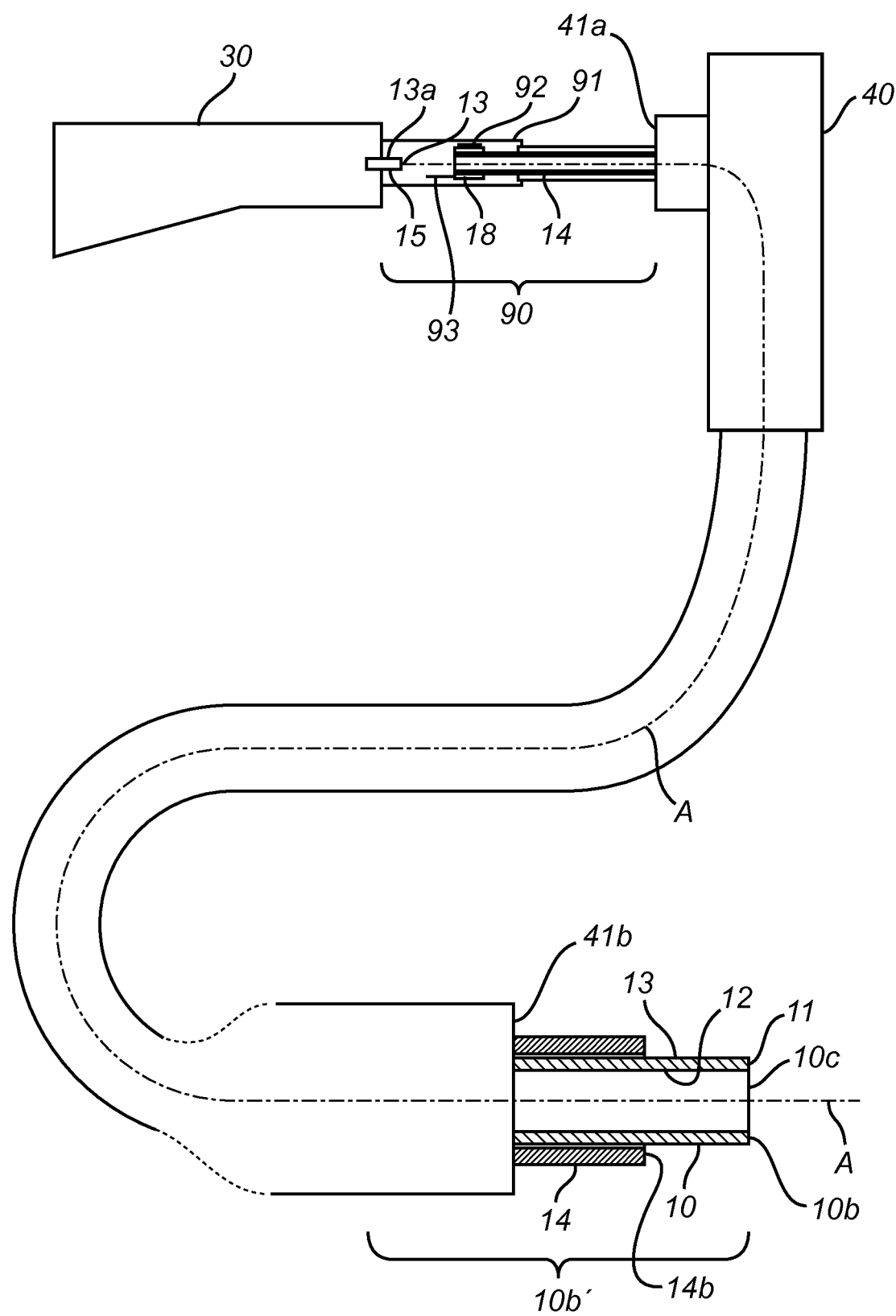
FIG. 17 is a schematic view disclosing the biopsy instrument of FIGS. 15 and 16 in use in an endoscope.
Figure 18:
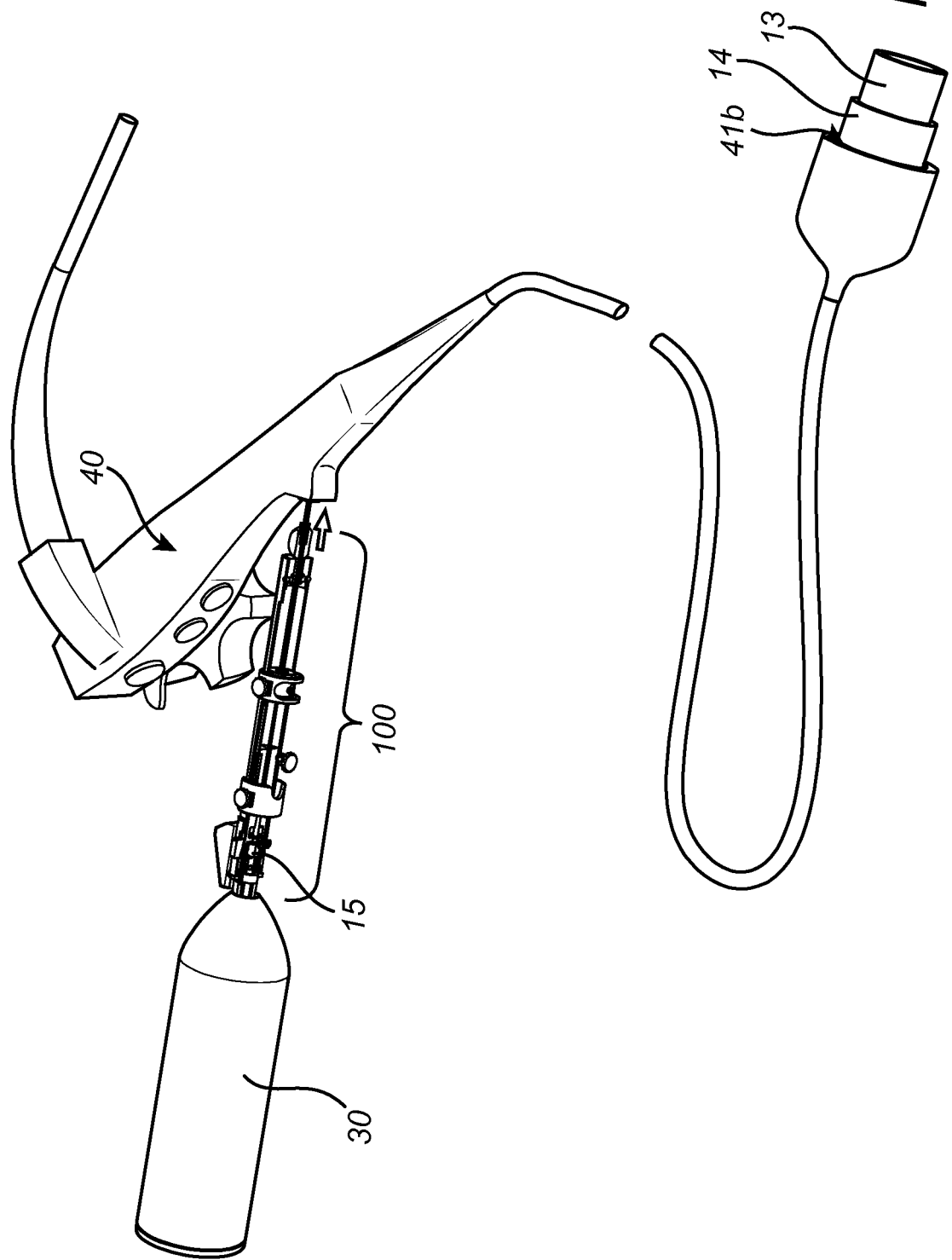
FIG. 18 is a schematic view disclosing a biopsy instrument of the same kind as in FIGS. 15-17 being connected to a variant of a telescope functionality between the motor and the biopsy instrument.
Figure 19:
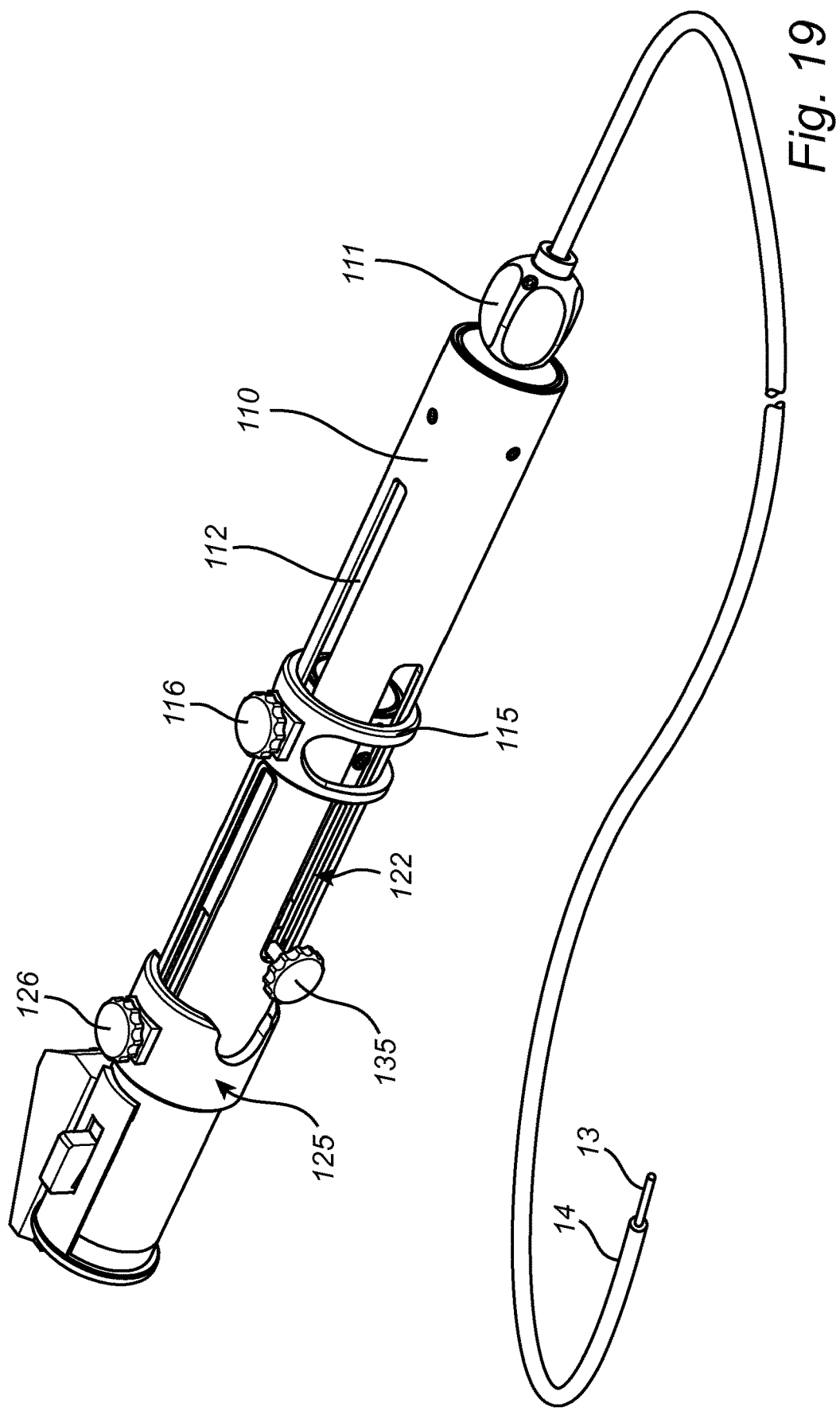
FIG. 19 discloses in more detail the telescope functionality shown in FIG. 18.
Figure 20:
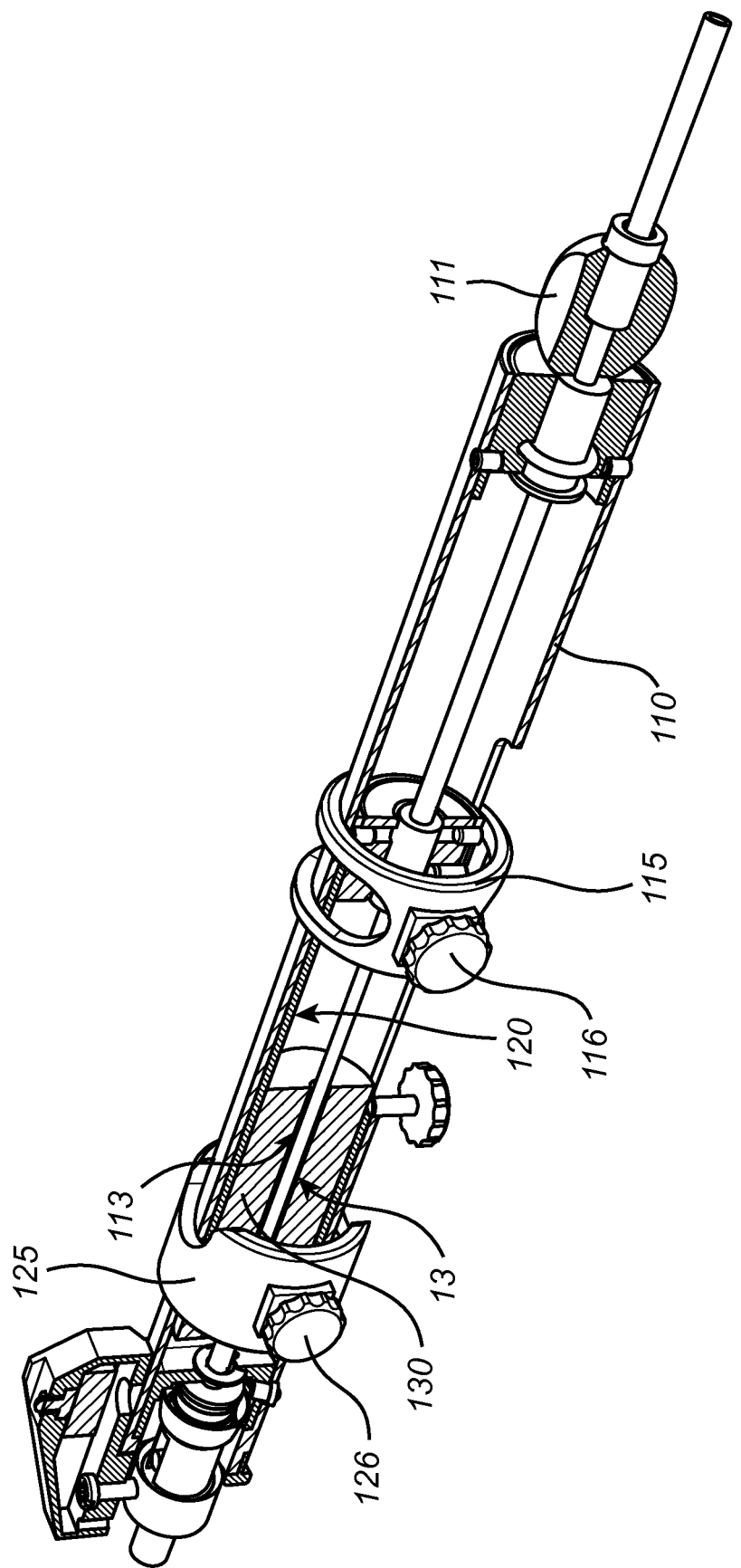
FIG. 20 is a cross-sectional view of the telescope functionality of FIGS. 18 and 19.
Figure 21:
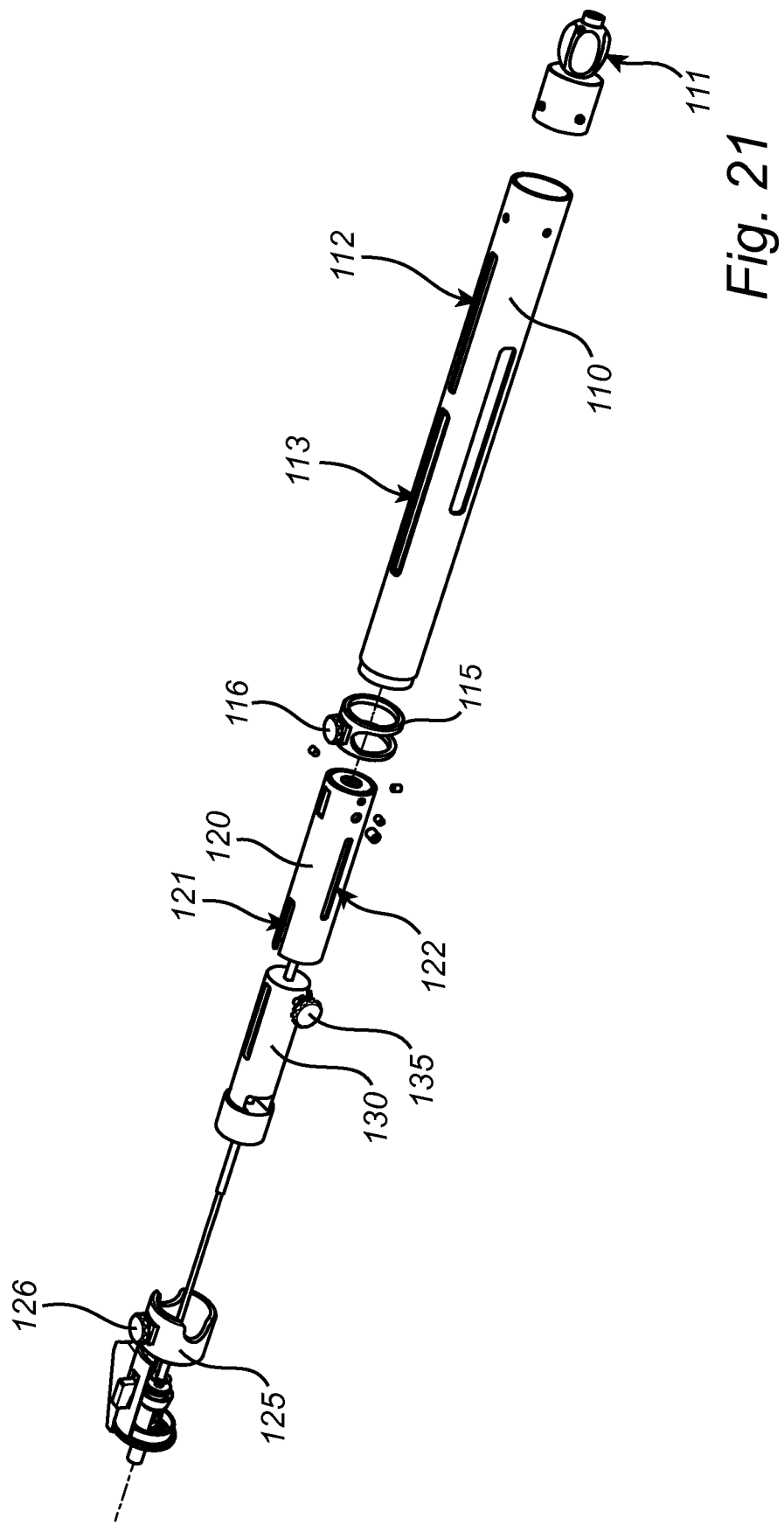
FIG. 21 is an exploded view of the telescope functionality of FIGS. 18-20.

In FIG. 17, there is shown a telescope functionality 90. The telescope functionality 90 may include a cover 91 at least partly but preferably completely covering the part of the biopsy instrument 1 between the access opening 41a and the manoeuvring unit 30. The telescope functionality 90 may have an adjustable length along the axis A such that a biopsy instrument 1 of a certain length may be used in different kinds of endoscopes 40 having slightly different lengths of the working channel 41 as measured between the access opening 41a and the distal opening 41b. The telescope functionality 90 may also provide a limit concerning a maximum extension of the distal end 10b of the elongated hollow tubular member 10 and/or a maximum extension of the distal end 14b of the outer elongated hollow tubular member 14. The telescope functionality 90 may also be provided with a locking member 92 by which the outer elongated hollow tubular member 14 is fixable relative to the endoscope 40 once the biopsy instrument 1 has been moved to the intended sample site. The telescope functionality 90 may also be provided with a locking member or abutment member 93 by which a maximum relative motion between the inner elongated hollow tubular member 13 and the outer elongated hollow tubular member 14 may be set, whereby a well-defined maximum sample depth may be provided for. It may be noted that in FIG. 17, the distal end of the endoscope 40 and the biopsy instrument 1 is for clarity reasons shown enlarged. However, in practice, the biopsy instrument 1 typically has the same diameter at the distal end portion 10b' as it has in other portions along the length of the biopsy instrument as e.g. shown in FIG. 19.

The telescopic functionality 100 shown in FIGS. 18-22 is especially configured for a biopsy instrument of the kind disclosed in FIGS. 15-16, i.e. a biopsy instrument having a non-rotating outer elongated hollow tubular member 14 and an inner elongated hollow tubular member 13 being rotatably arranged inside the outer elongated hollow tubular member 14. A proximal end of the telescopic functionality 100 is connected to the motor 30 and a distal end of the telescopic functionality 100 is connected to the endoscope 40. Different parts of the telescopic functionality 100 is connected to different parts of the biopsy instrument 1 as will be disclosed in more detail in the following.

The telescopic functionality 100 comprises a base sleeve 110. The base sleeve 110 is at a distal end thereof provided with a connector 111 by which the base sleeve 110 is configured to be connected to an insertion opening 41a of an endoscope 40. The motor 30 is configured to be connected to a proximal end of the base sleeve 110. The base sleeve 110 has a fixed length.

The telescopic functionality 100 further comprises an inner sleeve 120 which is slidably arranged inside the base sleeve 110. The inner sleeve 120 is connected to the outer elongated hollow tubular member 14 such that a sliding motion of the inner sleeve 120 in a distal direction relative to the base sleeve 110 results in that the outer elongated hollow tubular member 14 is moved in a distal direction relative to the endoscope. The telescope functionality 100 further comprises a first ring member 115 which is movably arranged around the base sleeve 110. The first ring member 115 is slidable back and forth along the base sleeve 110. It may be said to control the length of the outer elongated hollow tubular member 14 at the distal end of the endoscope 40. The first ring member 115 is provided with a connector 116, which in the disclosed embodiment is a screw and wedge, by which the first ring member 115 may be connected to the inner sleeve 120. In the disclosed embodiment, the screw is positioned in a threaded hole in the first ring member 115 and pushes a wedge into contact with the inner sleeve 120 when the screw is screwed into the threaded hole of the first ring member 115, which may be said to adjust the length of the outer elongated hollow tubular member 14 out of the endoscope distally. The connector 116 extends through a through-going long hole 112 formed in the wall of the base sleeve 110. By moving the first ring member 115 relative to the inner sleeve 120 to a desired location and connecting the first ring member 115 to the inner sleeve 120 at the desired location by activating the connector 116, in combination with the fact that the connector 116 extends through a long hole 112, it is possible to define to what extent the outer elongated hollow tubular member 14 may be moved out of the distal opening 41a of the endoscope 40. When the connector 116, which is connected to the inner sleeve 120 and which extends through the long hole 112, hits the distal end of the long hole 112, the connector 116 and thus also the first ring member 115 and the inner sleeve 120 is prevented from moving any further in the distal direction relative to the base sleeve 110.

The telescopic functionality 100 further comprises a central sleeve 130 which is slidably arranged inside the inner sleeve 120. The central sleeve 130 is connected to the inner elongated hollow tubular member 13 such that a sliding motion of the central sleeve 130 in a distal direction relative to the inner sleeve 120 results in that the inner elongated hollow tubular member 13 is moved in a distal direction relative to the outer elongated hollow tubular member 14. The inner elongated hollow tubular member 13 is rotatable inside the central sleeve 130. In the preferred embodiment, the inner elongated hollow tubular member 13 extends in a bore 131 through the central sleeve 130, the bore 131 having a diameter such there is a play between the inside of the bore 131 and the inner elongated hollow tubular member 13.

The telescope functionality 100 further comprises a second ring member 125 which is movably arranged around the base sleeve 110. The second ring member 125 is slidable back and forth along the base sleeve 110. The second ring member 125 is provided with a connector 126, which in the disclosed embodiment is a screw and wedge, by which the second ring member 125 may be connected to the central sleeve 130. In the disclosed embodiment, the screw is positioned in a threaded hole in the second ring member 125 and pushes a wedge into contact with the central sleeve 130 when the screw is screwed into the threaded hole of the first ring member 115. The connector 116 extends through a through-going long hole 113 formed in the wall of the base sleeve 110 and through a through-going long hole 121 in the inner sleeve 120. By moving the second ring member 125 relative to the central sleeve 130 to a desired location and connecting the second ring member 125 to the central sleeve 130 at the desired location by activating the connector 126, in combination with the fact that the connector 126 extends through the long hole 121 in the inner sleeve 120, it is possible to define to what extent the inner elongated hollow tubular member 13 may be moved out of the outer elongated hollow tubular member 14. When the connector 126, which is connected to the central sleeve 130 and which extends through the long hole 121, hits the distal end of the long hole 121, the connector 126 and thus also the second ring member 125 and the central sleeve 120 is prevented from moving any further in the distal direction relative to the inner sleeve 120.

The telescopic functionality 100 further comprises a connector 135 configured to interconnect the central sleeve 130 and the inner sleeve 120 at a desired relative position as seen along the direction along which the central sleeve 130 is slidable relative to the inner sleeve 120. In the disclosed embodiment the connector 135 is connected to the central sleeve 130 at a fixed position along said sliding direction. The connector 135 extends through a through-going long hole 122 formed in the wall of the inner sleeve 120 such that the connector 135 is accessible to a user and such that the central sleeve 130 may be slid relative to the inner sleeve 120 without the connector 135 preventing such sliding motion. The connector 136 is configured to be activated and interconnect the inner sleeve 120 to the central sleeve 130. In the disclosed embodiment, the connector 136 is screwed further into a threaded hole in the central sleeve 130 such that the head of the screw interacts with the walls of the inner sleeve 120 on the sides of the long hole 122.

It may be noted that it is conceivable that the telescopic functionality 100 may comprise the complete set of functionalities disclosed above and as shown in e.g. FIGS. 18-21. However, it is also conceivable that for certain applications it is desired that only one or two of the above described functionalities are present.

It is e.g. conceivable that for some applications it is preferred that it is possible to adjust the maximum length by which the outer elongated hollow tubular member 14 extends out of the distal opening 41*b* of the endoscope 40 in combination with a possibility to adjust the maximum length by which the inner elongated hollow tubular member 13 may be moved out of the outer elongated hollow tubular member 14. Such a set-up would typically be useful when there is a desire to perform a biopsy as indicated in FIGS. 3 and 4.

In an alternative embodiment there is only one setting available, namely the possibility to interconnect the inner sleeve 120 and the central sleeve 130. Such a set-up would typically be useful when there is a desire to perform a biopsy as indicated in FIGS. 13*a*-*b*. The user would set a fixed distance by which the inner elongated hollow tubular member 13 extends out of the outer elongated hollow tubular member 14 and thereafter the inner and outer elongated hollow tubular members 13, 14 would be moved together relative to the distal opening 41*b* of the endoscope 40, taking a superficial sample from the surface of the organ wall as e.g. shown in FIGS. 13*a*-*b* and 14*a*-*c*.

It may in this context also be noted that the telescopic functionality 90, 100 may be a separate part, i.e. being separate from and connectable to the endoscope 40, the biopsy instrument 1, and the motor 30. Alternatively, it may e.g. form part of the biopsy instrument 1 and as such have an interface for connection to a motor 30 and optionally also have an interface for connection to an endoscope 40.

In FIG. 22 there is schematically shown a design where the telescopic functionality 100 is separate from the biopsy instrument 1. The telescopic functionality 100 may be an integral part of the motor 30 but may alternatively be a separate part being connectable to the motor 30. The biopsy instrument 1 comprises an interface for connection to the telescopic functionality. The interface comprises a first connection member 13*e* which is connected to the inner elongated hollow tubular member 13 and which is configured to be connected to the central sleeve 130 of the telescopic functionality 100. The interface comprises a second connection member 14*e* which is connected to the outer elongated hollow tubular member 14 and which is configured to the connected to the inner sleeve 120.

Figure 5:
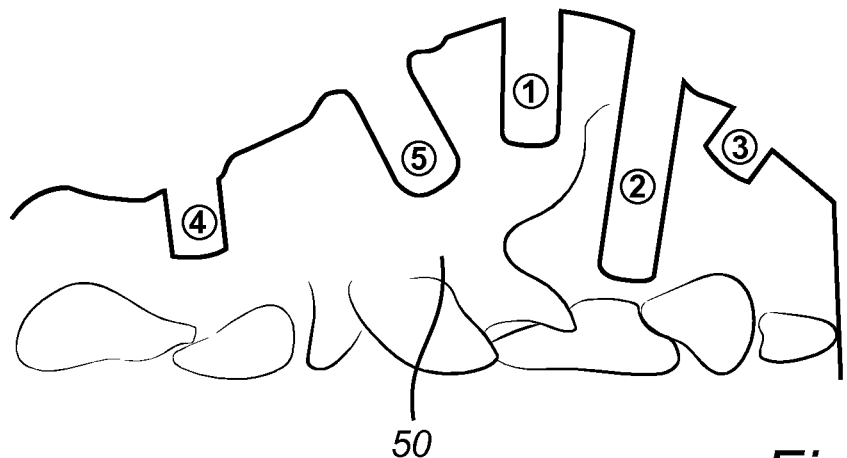
FIG. 5 shows the tissue after several samples has been acquired.

The biopsy instrument 1 may in actual biopsy sampling be used in accordance with a number of different methods. It may e.g. be used in accordance with one method where the biopsy instrument is used as shown in FIGS. 3-5, i.e. where the distal end 10*b* is advanced a distance into the tissue 50 and thereafter is retraced. However, the biopsy instrument 1 may in accordance with another method be used to move along the surface of the tissue 50 from which the biopsy is to be obtained as e.g. shown in FIGS. 13*a*-*b* and 14*a*-*c*. In the user method shown in FIGS. 3 and 4, the distal end 10*b* is fully inserted into the tissue 50 in the sense that the distal end 10*b* is inserted with the complete circumference C inserted into the tissue 50 whereby an adhesive force larger than breaking force needed to detach the core from the tissue is formed. In the method shown in FIGS. 13*a*-*b* and 14*a*-*c*, the distal end 10*b* is only partly inserted into the tissue 50 in the sense that the distal end 10*b* is inserted with only a portion of the complete circumference C being inserted into the tissue 50, as is shown in FIG. 14*a*. In FIG. 14*a* about half of the circumference C—the bottom half in FIG. 14*a*—is inserted into the tissue 50. As is shown in FIGS. 13*a*-*b*, the biopsy instrument 1 is in this method moved along the surface of the tissue 50 and cuts basically a continuous or at least semi-continuous groove 57 in the surface of the tissue 50.

In FIGS. 23 and 24 there is disclosed a variant of the biopsy instrument 1, where the outer elongated hollow tubular member 14 is a rigid hollow needle 14. The inner elongated hollow tubular member 13 is also a rigid hollow needle 13. As shown in FIG. 23, the inner rigid hollow needle 13 is configured to be positioned inside the outer rigid hollow needle 14. As shown in FIG. 24, the inner rigid hollow needle 13 has a length sufficient for it to be able to extend out of the distal opening of the outer rigid hollow needle 14. When handling the inner rigid hollow needle 13 and the outer rigid hollow needle 14, the inner rigid hollow needle 13 is preferably retracted such that it does not extend out of the distal opening of the outer rigid hollow needle 14 as shown in FIG. 25. In FIG. 25, the inner rigid hollow needle 13 and the outer rigid hollow needle 14 are about to be positioned into a manoeuvring unit 200 used to manoeuvre the inner rigid hollow needle 13 and the outer rigid hollow needle 14 in order to acquire a biopsy. The outer rigid hollow needle 14 may have an oblique end facilitating insertion of the outer rigid hollow needle 14 into the tissue to be sampled.

Moreover, it is also conceivable to provide an inner stylet inside the inner rigid hollow needle 13. The inner stylet may e.g. be provided with an oblique solid tip corresponding to the tip of the outer rigid hollow needle 14. The inner stylet may be used to cover the mouth of the inner rigid hollow needle 13 when biopsy instrument 1 is inserted into tissue to be sampled and to be removed partially or completely prior to rotation and/or insertion of said the inner rigid hollow needle 13 into the tissue.

Such a design with an inner stylet may be used in accordance with the following; the biopsy instrument 1 is moved, such as inserting the biopsy instrument 1 into the tissue through the skin or via a body cavity, to the sample site, with the inner stylet being positioned such that it during this movement of the biopsy instrument 1 closes the mouth of the inner rigid hollow needle. Thereafter, the inner stylet is moved in a proximal direction such that the mouth of the inner rigid hollow needle 13 is opened. The inner stylet is moved in the proximal direction at least a distance being sufficient to open up a distal portion of the inner rigid hollow needle 13 where the distal portion has a sufficient length to allow a sufficient amount of tissue to be retrieved into the inner rigid hollow needle 13. Thereafter, the inner rigid hollow needle 13 is advanced (and simultaneously being rotated) in the distal direction relative to the outer rigid hollow needle 14 and the sample is acquired. Thereafter, the inner rigid hollow needle 13 is retracted back into the outer rigid hollow needle 14 and the biopsy instrument 1 is retracted from the sample site. It may be noted that it is preferred that the inner stylet is moved in the proximal direction before the inner rigid hollow needle 13 is advanced but that it is sufficient that the inner stylet is moved in the proximal direction at the latest simultaneously as the inner rigid hollow needle 13 is being retracted back into the outer rigid hollow needle 14 such that the inner stylet does not push the sample inside the inner rigid hollow needle 13 out of the inner rigid hollow needle 13. After the biopsy instrument 1 has been removed from the sample site, the inner stylet may be used for harvesting the sample from the inner rigid hollow needle 13 by moving the inner stylet in the distal direction such that the inner stylet pushes the sample out of the inner rigid hollow needle 13. The inner stylet may be rigid. The inner stylet may be flexible and by guided by the inner rigid hollow needle.

It may be noted that the use of an inner stylet may also be applicable for a flexible biopsy instrument 1 configured for use with an endoscope 40. In such a case the inner stylet is also flexible and is guided by the inner elongated hollow tubular member 13.

As shown in FIG. 23, the inner rigid hollow needle 13 comprises an interface section 13e and the outer rigid hollow needle 14 also comprises an interface section 14e.

Figure 26A:
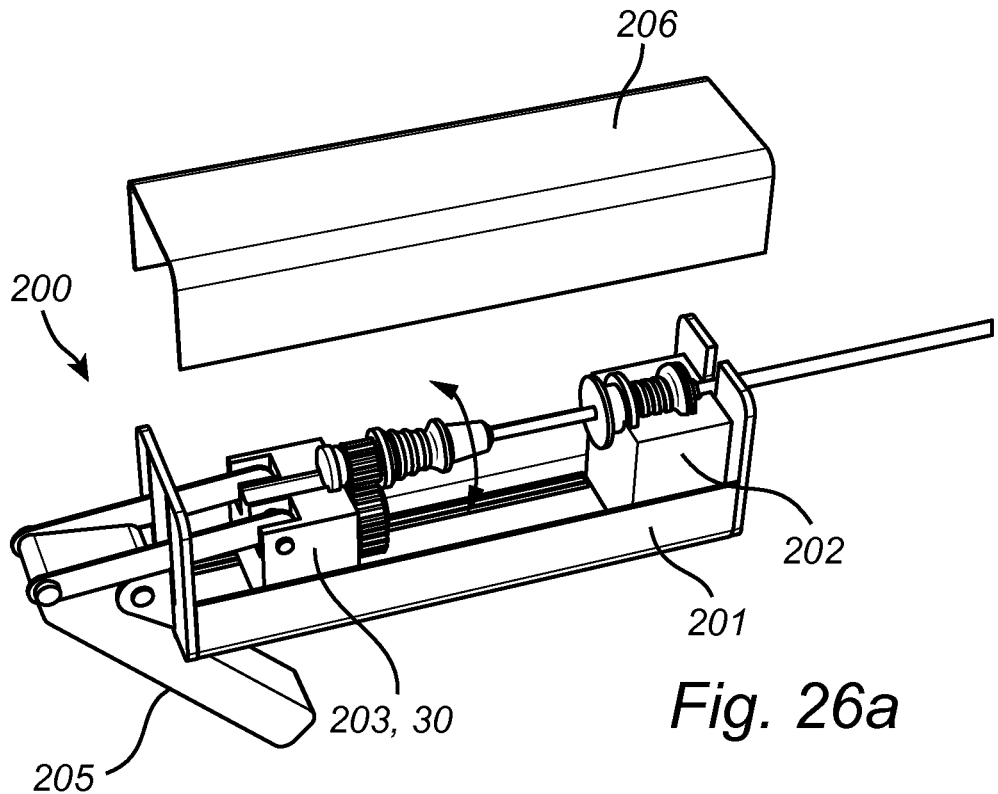
FIG. 26a discloses the needles positioned in the handle and in a state ready to acquire a biopsy sample.
Figure 26B:
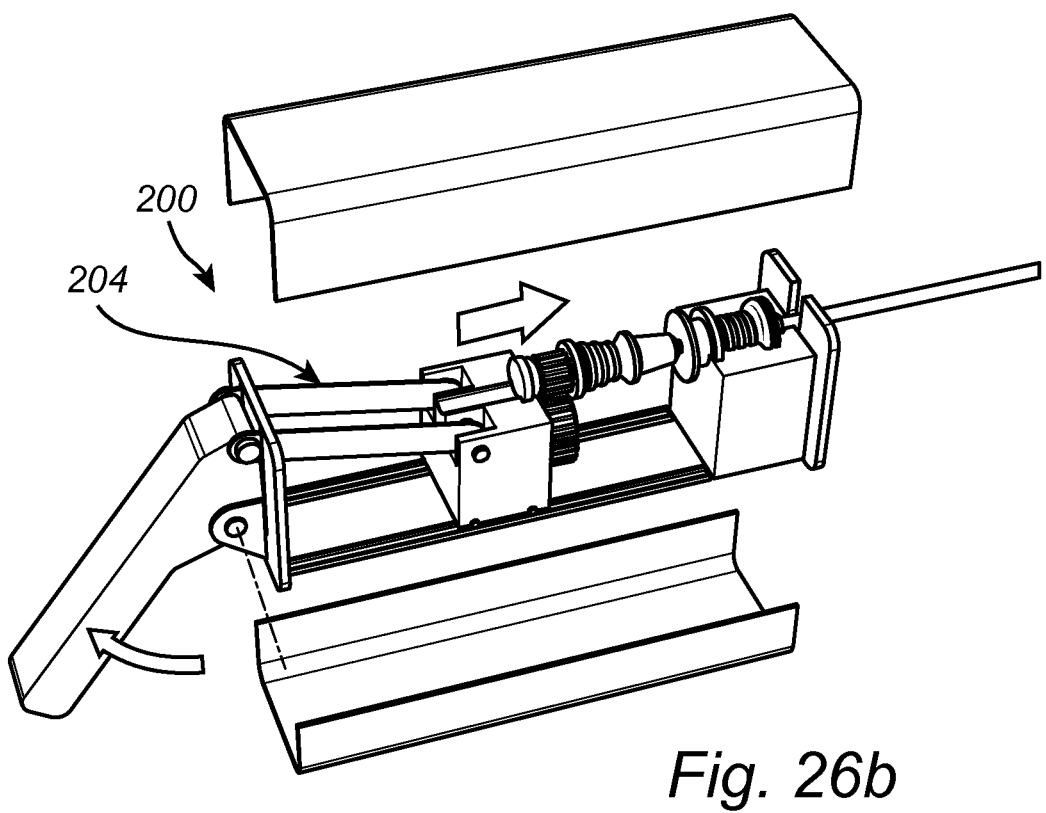
FIG. 26b discloses schematically operation of the handle to acquire a biopsy sample.

In FIGS. 26*a-b*, there is schematically shown example of a manoeuvring unit 200 suitable for making use of a biopsy instrument 1 of the basic type disclosed in FIGS. 23 and 24.

FIG. 26*a* discloses the needles positioned in the manoeuvring unit 200 and in a state ready to acquire a biopsy sample.

FIG. 26*b* discloses schematically operation of a handle 210 of the manoeuvring unit 200 to acquire a biopsy sample.

In more detail, the manoeuvring unit 200 comprises a base member 201 supporting the different components of the manoeuvring unit 200. The manoeuvring unit 200 comprises a support 202 configured to interact with the interface section 14e of the outer rigid hollow needle 14 and keep the outer rigid hollow needle 14 in position. Preferably, the outer rigid hollow needle 14 is kept fixed relative to the manoeuvring unit 200, i.e. the outer rigid hollow needle 14 is not moveable in the longitudinal direction and it is not rotatable relative to the manoeuvring unit 200.

The manoeuvring unit 200 further comprises a sled 202 configured to interact with the interface section 13e of the inner rigid hollow needle 13. The sled 203 also includes a motor 30 configured to rotate the inner rigid hollow needle 13 relative to the manoeuvring unit 200 and relative to the outer rigid hollow needle 14. The sled 203 is configured to be moved back and forth relative to the support 201 such that a distal end of the inner rigid hollow needle 13 may extend out the distal end of the outer rigid hollow needle 14 similarly as shown in FIG. 24 and such that it may be retracted again such that the distal end of the inner rigid hollow needle 13 is retracted back into the outer rigid hollow needle 14 such that the distal end of the inner rigid hollow needle 13 no longer extends out of the distal end of the outer rigid hollow needle 14. These manoeuvres of insertion and/or retraction may be manually or may be automated and electrically controlled by one or more buttons on the manoeuvring unit 200.

The sled 202 may be manoeuvred in the movement back and forth e.g. by a linkage 204 connected to a handle 205. By manoeuvring the handle 205 relative to the support 201, the sled 202 will be affected via the linkage 204. In a preferred embodiment, the manoeuvring unit 200 may comprise a second handle being fixed relative to the support 201, and the handle 205 shown in the FIGS. 26*a-b* may be moved towards such a fixed handle. For reasons of clarity, such fixed handle has been omitted.

The biopsy instrument 1 of FIGS. 23-24 is designed to be positioned inside the manoeuvring unit 200 such that the interface 14e of the outer rigid hollow needle 14 interacts with the support 202 and the interface 13e of the inner rigid needle 13 interacts with the sled 203 and the motor 30 on the sled 203. The manoeuvring unit 200 is configured to thereafter be closed by closing a lid 206 over the interface sections 13e and 14e of the inner and outer rigid hollow needles 13, 14 and the associated components 202, 203 of the manoeuvring unit 200. The lid 206 may be hinged relative to the base member 201. It may be connected to the base member 201 in other suitable manners, such as being slidably connected to the base member 201, being completely removable using a snap-fit connection or the like, etc.

The manoeuvring unit 200 is provided with a motor control, which e.g. may be a switch or button operated by the user or which may be an automatic controller connected to the manoeuvring of the sled 202 such that when the user begins to move the sled 202 the motor controller starts the motor 30 such that the inner rigid hollow needle 13 begins to rotate such that it rotates through-out the sample acquiring process.

After the sample has been acquired, the inner rigid hollow needle 13 is retracted into the outer rigid hollow needle 14 and the manoeuvring unit 200 is moved such that the inner and outer rigid hollow needles 13, 14 are moved out of the tissue being sampled.

The interface section 13e of the inner rigid hollow needle 13 may be provided with a plug or the like being capable of closing the proximal end of the inner rigid hollow needle 13. By the provision of such a plug, air trapped inside the inner rigid hollow needle 13 between the plug at the proximal end and the tissue at the distal end will form an air-cushion preventing excessive amounts of tissue being accumulated inside the inner rigid hollow needle 13. Alternatively, such a plug may be replaced by a mechanical blocking member positioned inside the inner rigid hollow needle 13. Such a mechanical blocking member is preferably inserted from the proximal end of the inner rigid hollow needle 13. The mechanical blocking member may, but need not, provide an air-tight connection with the inside to the inner rigid hollow needle 13. It may be noted that this provision of an air-plug or mechanical blocking member is not limited to the design of the biopsy instrument shown in FIGS. 23-26a-b. The concept of having an air-plug or mechanical blocking member is applicable to all the biopsy instruments disclosed.

The blocking member may during insertion be positioned such that it blocks or closes the mouth of the inner rigid hollow needle 13 or inner elongated hollow tubular member 13.

It may also be noted that the different variants of the biopsy instruments 1 may also be used for additional purposes. The inner hollow elongated tubular member 13, irrespective of if it is rigid or flexible, may be used as an introduction channel for the introduction of a guide wire. The outer hollow elongated tubular member 14, irrespective of if it is rigid or flexible, may be used as an introduction channel for the introduction of a guide wire. The guide wire may e.g. be used to insert a stent, a balloon, camera, injection tube or the like. The guide wire may also be used to insert a marker, such as a marker being visible on an X-ray image. The biopsy instrument 1 would in such a case typically be used in accordance with the following: first the instrument is inserted into the tissue and optionally a sample is also acquired; thereafter one of the elongated hollow tubular members 13, 14 is optionally removed completely (if a sample has been acquired, the inner hollow elongated tubular member 13 is removed such that the sample may be harvested); thereafter the guidewire is inserted via a part of the biopsy instrument 1 still being inserted to the intended position; thereafter all parts of the biopsy instrument is retracted while the guidewire remains extending to the intended position; thereafter the stent, balloon, marker is inserted or activated; and finally the guidewire is also retracted.

The invention claimed is:

1. A biopsy instrument comprising:
 a base member formed of an elongated hollow tube which extends from a proximal end to a distal end along a central geometrical axis, wherein the elongated hollow tube comprises:
 an inner elongated hollow tubular member, which has, at a distal portion thereof, a hollow elongated tubular sample acquiring portion having a smooth interior surface, and which is formed of a polymer based material, and
 an outer elongated hollow tubular member,
 wherein the inner elongated hollow tubular member is arranged inside the outer elongated hollow tubular member and is rotationally and translationally movable relative to the outer elongated hollow tubular member,
 wherein a distal end of the inner elongated hollow tubular member is intended to be at least partly inserted into a tissue from which a biopsy is to be obtained,
 wherein the inner elongated hollow tubular member is capable of transferring a force along the central geometrical axis such that a movement of the proximal end along the central geometrical axis is transferred to a movement of the distal end along the central geometrical axis, and of transferring a torque about the central geometrical axis such that a rotation and a torque applied by a motor at the proximal end about the central geometrical axis is transferred from the proximal end to the distal end thereby rotating the distal end about the central geometrical axis,
 wherein the inner elongated hollow tubular member is provided with a distally facing circular cutting edge defining a mouth of the distal end of the hollow tube,
 wherein the smooth interior surface is smooth to such an extent that when a reference biopsy is to be acquired, the distally facing circular cutting edge and the distal end of the inner elongated hollow tubular member is configured to be advanced along the central geometrical axis into a tissue while being rotated by being motor driven at its proximal end and thereby cutting a core of the tissue which, due to the advancement of the inner elongated hollow tubular member, enters relative to the inner elongated hollow tubular member through the mouth into the sample acquiring portion of the inner elongated hollow tubular member with a circumferential outer surface of the core at least partly abutting the smooth interior surface of the sample acquiring portion, where-after the inner elongated hollow tubular member is retracted from the tissue while being rotated by being motor driven at its proximal end whereby the core of the tissue is detached from the tissue by a pulling force due to the retraction of the hollow tube and due to an adhesive force formed due to the smooth surface and the presence of liquid in the tissue at an interface between the smooth interior surface and the circumferential outer surface of the core which force keeps the core inside the sample acquiring portion having the smooth interior surface,
 wherein the distally facing circular cutting edge has as seen along a circumference of the mouth, a straight-line configuration, and the mouth defines a plane having a normal parallel to the extension of the central geometrical axis as the central geometrical axis passes through said plane of the mouth,
 wherein the inner elongated hollow tubular member is airtight such that suction is provided at an interface between the inside wall of the inner elongated hollow tubular member and a core of the tissue sample when the inner elongated hollow tubular member is retracted, and
 wherein the inner elongated hollow tubular member is rotated in the same direction during advancement and retraction.

2. The biopsy instrument according to claim 1, further comprising a telescope functionality being configured to be positioned between an access opening of an endoscope and a maneuvering unit, wherein the telescope functionality has an adjustable length along the central geometrical axis.

3. The biopsy instrument according to claim 2, wherein the telescope functionality provides a limit concerning a maximum extension of the distal end of the inner elongated hollow tubular member.

4. The biopsy instrument according to claim 2, wherein the telescope functionality provides a limit concerning a maximum extension of a distal end of the outer elongated hollow tubular member.

5. The biopsy instrument according to claim 1, wherein the base member is, from a bending perspective, flexible such that the base member is capable of being inserted into and be used together with an endoscope.

6. The biopsy instrument according to claim 1, wherein the hollow elongated tubular sample acquiring portion having a smooth interior surface has a length along the central geometrical axis being at least 10 times an inner diameter of the inner elongated hollow tubular member.

7. The biopsy instrument according to claim 1, wherein the inner elongated hollow tubular member is airtight at least along the length of the tubular sample acquiring portion along the central geometrical axis.

8. The biopsy instrument according to claim 1, wherein the inner elongated hollow tubular member has at a proximal end thereof a connector for connection to a motor, the connector being capable of transferring said force and movement along the central geometrical axis and said rotation and torque.

9. A kit of parts comprising:
   a biopsy instrument according to claim 1, and
   a maneuvering unit comprising a motor,
   wherein the biopsy instrument at its proximal end is connectable to the motor such that rotation and torque may be applied by the motor to the proximal end of the base member and transferred to the distal end of the base member.

10. A method of acquiring a biopsy, the method comprising:
   connecting a proximal end of a biopsy instrument to a maneuvering unit having a motor,
   moving a distal end of the biopsy instrument to a position where a tissue sample is to be acquired,
   activating the motor such that rotation is transferred to the distal end of the biopsy instrument,
   advancing the distal end, which at least a distal end portion of the biopsy instrument is shaped as an elongated hollow tube having a distally facing circular cutting edge defining a mouth of the distal end of the hollow tube, into the tissue from which a tissue sample is to be obtained while the distal end is being rotated by the motor thereby cutting a core of the tissue which, due to the advancement of the hollow tube, enters relative to the hollow tube through the mouth into a sample acquiring portion of the hollow tube,
   retracting the distal end out of the tissue while the distal end is being rotated by the motor with a circumferential outer surface of the core at least partly abutting a smooth interior surface of a hollow elongated tubular sample acquiring portion being provided at a distal portion of the hollow tub,
   whereby the core of the tissue is detached from the tissue by a pulling force due to the retraction of the hollow tube and due to an adhesive force formed at an interface between the smooth interior surface and the circumferential outer surface of the core which force keeps the core inside the sample acquiring portion having the smooth interior surface,
   wherein the distally facing circular cutting edge has as seen along a circumference of the mouth, a straight-line configuration, and the mouth defines a plane having a normal parallel to the extension of the central geometrical axis as the central geometrical axis passes through said plane of the mouth,
   wherein the inner elongated hollow tubular member is airtight such that suction is provided at an interface between the inside wall of the inner elongated hollow tubular member and a core of the tissue sample when the inner elongated hollow tubular member is retracted, and
   wherein the inner elongated hollow tubular member is rotated in the same direction during the advancing and the retracting.

* * * * *